US008481734B2

(12) United States Patent
Dorshow et al.

(10) Patent No.: US 8,481,734 B2
(45) Date of Patent: *Jul. 9, 2013

(54) PYRAZINE DERIVATIVES AND USES THEREOF, INCLUDING IN MEDICAL IMAGING AND VISUALIZATION APPLICATIONS

(75) Inventors: Richard B. Dorshow, St. Louis, MO (US); John Freskos, Clayton, MO (US); William L. Neumann, St. Louis, MO (US); Amruta Reddy Poreddy, St. Louis, MO (US); Raghavan Rajagopalan, St. Peters, MO (US)

(73) Assignee: Medibeacon Development LLC, St. Louis, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/351,891

(22) Filed: Jan. 12, 2009

(65) Prior Publication Data

US 2010/0021382 A1 Jan. 28, 2010

Related U.S. Application Data

(63) Continuation of application No. 12/349,773, filed on Jan. 7, 2009, now abandoned.

(60) Provisional application No. 61/080,207, filed on Jul. 11, 2008, provisional application No. 61/082,296, filed on Jul. 21, 2008.

(51) Int. Cl.
*C07D 241/02* (2006.01)

(52) U.S. Cl.
USPC ........................................................ 544/407

(58) Field of Classification Search
USPC ........................................................ 544/407
See application file for complete search history.

(56) References Cited

U.S. PATENT DOCUMENTS

| 3,573,305 A * | 3/1971 | Cragoe et al. ................. 544/407 |
| 3,959,277 A | 5/1976 | Donald |
| 2005/0137234 A1 | 6/2005 | Bressi et al. |

FOREIGN PATENT DOCUMENTS

| GB | 2 139 213 | 11/1984 |
| WO | WO 2006/003378 | 1/2006 |
| WO | WO 2006/071759 | 7/2006 |
| WO | WO 2007/149479 | 12/2007 |

OTHER PUBLICATIONS

Jordan, V. C. Nature Reviews: Drug Discovery, 2, 2003, 205.*
Dorwald, F. Zaragoza. Side Reactions in Organic Synthesis: A Guide to Successful Synthesis Design, Weinheim: Wiley-VCH Verlag GmbH & Co. KGaA, 2005, Preface.*
Abdel-Magid et al., "Reductive Amination of Aldehydes and Ketones with Sodium Triacetoxyborohydride. Studies on direct and Indirect Reductive Amination Procedures", J. Org. Chem., 1996, 61, pp. 3849-3862 XP 002217704.
Jeanjot et al., "N-(Alkyl)-2-amino-1,4-pyrazine Derivatives: Synthesis and Antioxidative Properties of 3- and 3,5-p-Hydroxyphenyl-Substituted Compounds", Synthesis, 2003, No. 4, pp. 513-522.
Teranishi, "Effect of conformation on the dhemiluminescence efficiency of light-producing 2-methy1-6-(4-methoxyphenyl)imidazo[1,2-a]pyrazin-3(7H)-ones", Luminescence, 2001, 16, pp. 367-374.
Abdel-Magid et al., "Reductive Amination of Aldehydes and Ketones with Sodium Triacetoxyborohydride. Studies on direct and Indirect Reductive Amination Procedures", J. Org. Chem., 1996, 61, pp. 3849-3862.
Kim et al., "Self-Assembling of Aminopyrazine Fluorescent Dyes and Their Solid State Spectra", Dyes and Pigments, 1998, 39(4), pp. 341-357.
Kim et al., "Self-Assembling of Aminopyrazine Fluorescent Dyes and Their Solid State Spectra, Part 2", Dyes and Pigments, 1999, 41, pp. 183-191.
Shirai et al., "Syntheses and Fluorescent Properties of 2,5-Diamino-3,6-dicyanopyrazine Dyes", Dyes and Pigments, 1998, 39(1), pp. 49-68.
Rabito et al., "Renal Function in Patients at Risk of Contrast Material-induced Acute Renal Failure: Noninvasive, Real-Time Monitoring", Radiology, 1993, 186, pp. 851-854.
Tilney et al., "Acute Renal Failure in Surgical Patients: Causes, Clinical Patterns, and Care", Surgical Clinics of North America, vol. 63, No. 2, Apr. 1983, pp. 357-377.
Vanzee et al., "Renal Injury Associated with Intravenous Pyelography in Nondiabetic and Diabetic Patients", Annals of Internal Medicine, 1978, 89, pp. 51-54.
Lundqvist et al., "Iohexol Clearance for Renal Function Measurement in Dynaecologic Cancer Patients", Acta Radiologica, 1996, 39, pp. 582-586.
Guesry et al., "Measurement of glomerular filtration rate by fluorescent excitation of non-radioactive meglumine iothalamate", Clinical Nephrology, 1975, 3(4), pp. 134-138.

(Continued)

*Primary Examiner* — Douglas M Willis
(74) *Attorney, Agent, or Firm* — Gale Starkey; Dennis A. Bennett

(57) ABSTRACT

Disclosed herein are pyrazine derivatives of Formula I:

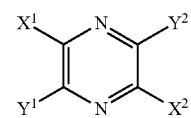

Formula I; wherein each of $X^1$ and $X^2$ is independently —$CONR^7R^9$; and each of $Y^1$ and $Y^2$ is independently —$NR^{48}R^{49}$; and methods of using the same. The disclosed pyrazine derivatives include those having urea, amide, sulfonamide, thiourea, and/or carbamate substituents. Among the various aspects of the present invention are pyrazine derivatives that may be detected in vivo and used in a number of medical procedures (e.g., renal function monitoring). Without being bound by a particular theory, the pyrazine derivatives described herein may be designed to be hydrophilic, thus allowing for rapid renal clearance for continuous monitoring of renal function.

19 Claims, 3 Drawing Sheets

OTHER PUBLICATIONS

Baker et al., "Epidemiology of Trauma Deaths", American Journal of Surgery, vol. 140, Jul. 1980, pp. 144-150.

Regel et al., "Treatment Results of Patients with Multiple Trauma: An Analysis of 3406 Cases Treated between 1972 and 1991 at a German Level 1 Trauma Center", The Journal of Trauma: Injury, Infection and Critical Care, vol. 38, No. 1, Jan. 1995.

Dodge et al., "Comparison of Endogenous Creatinine Clearance With Inulin Clearance", Amer. J. Dis. Child, vol. 113, Jun. 1967, pp. 683-692.

Brochner-Mortensen et al., "Renal Inulin Clearance versus Total Plasma Clearance of $^{51}$Cr-EDTA", May 1, 1969, pp. 301-305.

White et al., "Estimating Glomerular Filtration Rate in Kidney Transplantation: A Comparison between Serum Creatinine and Cystatin C-Based Methods", J. Am. Soc. Nephrol, 2005, 16, pp. 3763-3770.

Choyke et al., "Hydrated clearance of gadolinium-DTPA as a measurement of glomerular filtration rate", Kidney International, vol. 41, 1992, pp. 1595-1598.

Tweedle et al., "A Noninvasive Method for Monitoring Renal Status at Bedside", Investigative Radiology, vol. 32, No. 12, 1997, pp. 802-805.

Lewis et al., "Comparative Evaluation of Urographic contrast Media, Inulin, and $^{99m}$Tc-DTPA Clearance Methods for Determination of Glomerular Filtration Rate in Clinical Transplantation", Transplantation, vol. 48, No. 5, Nov. 1989, pp. 790-796.

Muller-Suur et al., "Glomerular Filtration and Tubular Secretion of MAG-3 in the Rat Kidney",The J. of Nuc. Med., 30(12), Dec. 1989, pp. 1986-1991.

Sekar, "Pyrazine dyes: An update", Colourage, Jan. 1999, pp. 40-44.

Yamaoka et al., "Distribution and Tissue Uptake of Poly(ethylene glycol) with Different Molecular Weights after Intravenous Administration to Mice", Journal of Pharmaceutical Sciences, vol. 83, No. 4, Apr. 1994, pp. 601-606.

Dorshow et al., "Noninvasive Fluorescence Detection of Hepatic and Renal Function", Journal of Biomedical Optics, Jul. 1998, vol. 3, No. 3, pp. 340-345.

Dorshow et al. (2008), "New optical probes for the continuous monitoring of renal function," In "Molecular Probes for Biomedical Applications II," S. Achilefu, D.J. Bornhop, R. Raghavachari: eds., Proc. of SPIE, vol. 6867, 68670C, pp. 68670C-1-68670C-11.

Roch-Ramel et al. (1992), "Renal excretion and tubular transport of organic anions and cations" In: Handbook of physiology, section 8: renal physiology. Windhager EE (editor), Oxford University Press, New York/Oxford, pp. 2189-2262.

Roch-Ramel et al. (2003), "Renal handling of drugs and xenobiotics," M.E. De Broe, G.A. Porter, W.M. Bennet & G.A. Verpooten (Editors), Clinical Nephrotoxins, $2^{nd}$ Edition, pp. 21-46.

Rao et al. (Apr. 1969), The Synthesis of Pyrazines, Pyrazino [2,3-$d$] pyridazines and a Dipyridazino [4,5-$b$:4',5'-$e$] pyrazine, Journal of Heterocyclic Chemistry, Issue 2, pp. 255-258.

Takahashi et al. (1974), "Synthesis and Fluorescence of 2, 5-Distyryl-3, 6-bis(dimethylcarbamoyl)pyrazine Derivatives," Department of Synthetic Chemistry, China University; Yayoi-cho, Chiba-shi 280 Japan; (11), pp. 2123-2126.

Official Report issued on Apr. 22, 2010 for corresponding Australian Patent Application No. 2008237606.

Official Report issued on Apr. 22, 2010 for corresponding Australian Patent Application No. 2008237601.

An English translation of the Office Action issued on Jan. 12, 2011 for corresponding Chinese Patent Application No. 200810185844.2.

* cited by examiner

US 8,481,734 B2

PYRAZINE DERIVATIVES AND USES THEREOF, INCLUDING IN MEDICAL IMAGING AND VISUALIZATION APPLICATIONS

RELATED APPLICATIONS

This application is a continuation of U.S. patent application Ser. No. 12/349,773 filed on 7 Jan. 2009 and entitled "Methods of Producing N,N-Alkylated Diaminopyrazines," which claims priority to U.S. provisional application Ser. Nos. 61/080,207 and 61/082,296 filed on 11 Jul. 2008 and 21 Jul. 2008 (respectively), both of which are entitled "Pyrazine Derivatives, Methods of Use, and Methods for Preparing Same."

FIELD

The present invention relates to pyrazine derivatives, such as those capable of absorbing and/or emanating spectral energy in the visible and/or near infrared spectrum. In addition, the present invention relates to methods of using non-radioactive, exogenous agents (e.g., the previously mentioned pyrazine derivatives) in the monitoring of renal function. Methods of making pyrazine derivatives are also provided.

INTRODUCTION

The ability to continuously monitor renal function via the glomerular filtration rate (GFR) in the clinic is currently an unmet medical need.[1-5] Monitoring of renal function is important to reduce the risk of acute renal failure caused by clinical, physiological, and pathological conditions. It is particularly important in the cases of critically ill or injured patients, since these patients tend to frequently face the risk of multiple organ failure and death.[6, 7]

Currently, the most common method of gauging renal function is serum creatinine measurement at frequent intervals over a 24-hour period.[8,9] The results are often misleading, given that the concentration is affected by age, hydration state, renal perfusion, muscle mass, diet and many other anthropometric and clinical variables.[10]

An accurate, real-time measure of renal excretion rate using exogenous markers would represent a substantial improvement over current practices. It would also be desirable to provide a process that allows for less subjective interpretation based upon age, muscle mass, blood pressure, etc. Exogenous markers such as insulin, iothalamate, $^{51}$Cr-EDTA, Gd-DTPA, and $^{99m}$Tc-DTPA may be used to measure GFR.[11-13] Other markers such as $^{123}$I and $^{125}$I labeled o-iodohippurate or $^{99m}$TcMAG$_3$ may be used to assess the tubular secretion process.[14] Unfortunately, these markers and methods suffer from drawbacks such as the use of radioactivity and/or ionizing radiation. These limitations make them undesirable for a number of medical uses (e.g., real-time, bedside renal function monitoring).

SUMMARY

Among the various aspects of the present invention are pyrazine derivatives that may be detected in vivo and used in a number of medical procedures (e.g., renal function monitoring). Without being bound by a particular theory, the pyrazine derivatives described herein may be designed to be hydrophilic and/or have rigid functionality, thus allowing for rapid renal clearance while providing desired pharmacokinetic properties for monitoring renal function.

A first aspect of the invention is directed to pyrazine derivatives, each of which has a pyrazine ring. A carbon of the pyrazine ring has a substituent bonded thereto that includes a group selected from urea, amide, sulfonamide, thiourea, carbamate, or any combination thereof. In this pyrazine derivative, at least one occurrence of an above-mentioned group is separated from the carbon of the pyrazine ring to which the substituent is bonded by at least two atoms. For example, the substituent may include one of the aforementioned groups that is bonded directly to the carbon as long as the substituent also has at least one occurrence of one of the aforementioned groups that is separated from the carbon of the pyrazine ring to which the substituent is bonded by at least two atoms.

With regard to the pyrazine derivatives of the first aspect of the invention, at least one occurrence of the group may be separated from the carbon of the pyrazine ring to which the substituent is bonded by other appropriate atom spacings. For instance, in some embodiments, at least one occurrence of an aforementioned group is separated from the carbon of the pyrazine ring to which the substituent is bonded by at least three atoms. In other embodiments, at least one occurrence of an aforementioned group is separated from the carbon of the pyrazine ring to which the substituent is bonded by at least four atoms. In still other embodiments, at least one occurrence of an aforementioned group is separated from the carbon of the pyrazine ring to which the substituent is bonded by at least five atoms. And in even other embodiments, at least one occurrence of an aforementioned group is separated from the carbon of the pyrazine ring to which the substituent is bonded by at least six atoms.

Still referring to the pyrazine derivatives of the first aspect of the invention, in some embodiments, each occurrence of an aforemention group may be separated from the carbon of the pyrazine ring to which the substituent is bonded by at least two atoms. In other words, in these embodiments, no portion of a urea, amide, sulfonamide, thiourea, carbamate, or any combination thereof is located within two atoms of the carbon (of the pyrazine ring) to which the substituent is bonded. In some embodiments, each occurrence of the group may be separated from the carbon of the pyrazine ring to which the substituent is bonded by at least three, at least four, at least five, or even at least six atoms.

In some embodiments of the first aspect, each of the four carbons of the pyrazine ring has a substituent bonded thereto. In such embodiments, each occurrence of an aforemention group of any of the four substituents may be separated from the carbon of the pyrazine ring to which the substituent is bonded by at least two atoms. In other embodiments, each occurrence of an aforementioned group of any of the four substituents may be separated from the carbon of the pyrazine ring to which the substituent is bonded by at least three, at least four, at least five, or even at least six atoms.

Still referring to pyrazine derivatives of the first aspect, in some embodiments, a first carbon of the pyrazine ring has a first substituent bonded thereto that includes a first group selected from urea, amide, sulfonamide, thiourea, carbamate, and any combination thereof. Further, a second carbon of the pyrazine ring has a second substituent bonded thereto that includes a second group selected from urea, amide, sulfonamide, thiourea, carbamate, and any combination thereof. In such embodiments, the first group is separated from the first carbon of the pyrazine ring by at least two atoms, and the second group is separated from the second carbon of the pyrazine ring by at least two atoms. The first group may be the same as or different from the second group. For instance, in the case that the first group is the same as the second group, the first group and the second may each be an amide. As another example, the first group and the second group may each be a urea. In some embodiments, the first substituent that is bonded to the first carbon of the pyrazine ring may be the same as or different from the second substituent.

The first carbon and the second carbon may be located in any appropriate positions along the pyrazine ring. For instance, in some embodiments, the first carbon of the pyrazine ring is para to the second carbon of the pyrazine ring. In other embodiments, the first carbon of the pyrazine ring is meta to the second carbon of the pyrazine ring.

In embodiments having a first substituent that is bonded to a first carbon and a second substituent that is bonded to a second carbon, the first and second substituents may include any of a number of other appropriate groups besides each including at least one of the groups mentioned above (e.g., urea, amide, sulfonamide, thiourea, carbamate, and/or any combination thereof). For instance, in some embodiments, at least one of the first and second substituents may include at least one polyethylene glycol (PEG) unit (e.g., a plurality of PEG units). Incidentally, a "PEG unit" herein refers to a $CH_2CH_2O$ unit. In some embodiments, each of the first and second substituents comprises at least one PEG unit. For example, in some embodiments, the first substituent may include a plurality of PEG units, and the second substituent may also include a plurality of PEG units.

A second aspect of the invention is directed to pyrazine derivatives, each of which includes a pyrazine ring that comprises a first carbon, a second carbon, a third carbon, and a fourth carbon. The first carbon has a first substituent bonded thereto, the second carbon has a second substituent bonded thereto, the third carbon has a third substituent bonded thereto, and the fourth carbon has a fourth substituent bonded thereto. Each of the first, second, third, and fourth substituents includes a group selected from urea, amide, sulfonamide, thiourea, carbamate, and any combination thereof.

With regard to the second aspect of the invention, the structure of a given substituent may be same as or different from one or more other substituents of the pyrazine derivative. For instance, in some embodiments, the first and second substituents are the same, and the third and fourth substituents are the same but different from the first and second substituents. In such embodiments, the first and second carbons may be para to each other (which means the third and fourth carbons would also be para to each other), or the first and second carbons may be meta to each other (which means the third and fourth carbons would also be meta to each other).

In some embodiments of pyrazine derivatives of the second aspect, each of the first and second substituents includes an amide. For instance, in some embodiments, each of the first, second, third, and fourth substituents includes an amide.

Some embodiments of the pyrazine derivatives of the second aspect may include at least two of the first, second, third, and fourth substituents having at least one PEG unit. For instance, in some embodiments, each of the first and second substituents comprises at least one PEG unit. As another example, each of the first, second, third, and fourth substituents may include at least one PEG unit.

Yet a third aspect of the invention is directed to pyrazine derivatives, each of which includes a pyrazine ring. A carbon of the pyrazine ring has a substituent bonded thereto that includes a urea group. Further, this urea group is separated from the carbon of the pyrazine ring to which the substituent is bonded by at least two atoms. So, at least in theory, the substituent may include one urea that is bonded directly to the carbon of the pyrazine ring as long as the substituent also includes at least one other urea that is separated from the carbon of the pyrazine ring to which the substituent is bonded by at least two atoms. As another example, one substituent may include a urea that is bonded directly to one carbon of the pyrazine ring, and another substituent may include another urea that is separated from the respective carbon of the pyrazine ring to which that substituent is bonded by at least two atoms.

With regard to the pyrazine derivatives of the third aspect, at least one occurrence of a urea group may be separated from the carbon of the pyrazine ring to which the substituent is bonded by other appropriate atom spacings. For instance, in some embodiments, at least one occurrence of a urea group is separated from the carbon of the pyrazine ring to which the corresponding substituent is bonded by at least three atoms. In other embodiments, at least one occurrence of a urea group is separated from the carbon of the pyrazine ring to which the corresponding substituent is bonded by at least four atoms. In still other embodiments, at least one occurrence of a urea group is separated from the carbon of the pyrazine ring to which the corresponding substituent is bonded by at least five atoms. And in even other embodiments, at least one occurrence of a urea group is separated from the carbon of the pyrazine ring to which the corresponding substituent is bonded by at least six atoms.

Still referring to the pyrazine derivatives of the third aspect of the invention, in some embodiments, the substituent includes multiple occurrences of urea groups, and each occurrence of a urea group is separated from the carbon of the pyrazine ring to which the substituent is bonded by at least two atoms. In other words, in these embodiments, no portion of a urea group is located within two atoms of the carbon (of the pyrazine ring) to which the substituent is bonded. In some substituents that include multiple occurrences of urea groups, each occurrence of a urea group may be separated from the carbon of the pyrazine ring to which the substituent is bonded by at least three, at least four, at least five, or even at least six atoms.

Still referring to the third aspect, in some embodiments, each of the four carbons of the pyrazine ring has a substituent bonded thereto. In such embodiments, each occurrence of a urea group of any of the four substituents may be separated from the carbon of the pyrazine ring to which the substituent is bonded by at least two atoms. In other embodiments, each occurrence of a urea of any of the four substituents may be separated from the carbon of the pyrazine ring to which the substituent is bonded by at least three, at least four, at least five, or even at least six atoms.

In pyrazine derivatives of the third aspect, the substituent(s) may include any of a number of other appropriate groups besides at least one urea. For instance, in some embodiments, the substituent that includes the urea may also include at least one PEG unit (e.g., a plurality of PEG units). In some embodiments, each of a plurality (e.g., two, three, or four) of substituents, each of which is bound to a different carbon of the pyrazine ring, may include at least one PEG unit. For example, in some embodiments, a first substituent bound to a first carbon of the pyrazine ring may include a urea and plurality of PEG units, and a second substituent bound to a second carbon of the pyrazine ring may also include a urea and a plurality of PEG units. In such embodiments, the first and second carbons may be either meta or para to each other.

Still a fourth aspect of the invention is directed to pyrazine derivatives, each of which includes a pyrazine ring. A carbon of the pyrazine ring has a substituent bonded thereto that includes an amide group. Further, this amide group is separated from the carbon of the pyrazine ring to which the substituent is bonded by at least two atoms. So, at least in theory, the substituent may include one amide that is bonded directly to the carbon of the pyrazine ring as long as the substituent also includes at least one other amide that is separated from the carbon of the pyrazine ring to which the substituent is bonded by at least two atoms. As another example, one substituent may include an amide that is bonded directly to one carbon of the pyrazine ring, and another substituent may include another amide that is separated from the respective carbon of the pyrazine ring to which that substituent is bonded by at least two atoms.

With regard to the pyrazine derivatives of the fourth aspect, at least one occurrence of an amide group may be separated from the carbon of the pyrazine ring to which the substituent is bonded by other appropriate atom spacings. For instance, in some embodiments, at least one occurrence of an amide group is separated from the carbon of the pyrazine ring to which the corresponding substituent is bonded by at least three atoms. In other embodiments, at least one occurrence of an amide group is separated from the carbon of the pyrazine ring to which the corresponding substituent is bonded by at least four atoms. In still other embodiments, at least one occurrence of an amide group is separated from the carbon of the pyrazine ring to which the corresponding substituent is bonded by at least five atoms. And in even other embodiments, at least one occurrence of an amide group is separated from the carbon of the pyrazine ring to which the corresponding substituent is bonded by at least six atoms.

Still referring to the pyrazine derivatives of the fourth aspect of the invention, in some embodiments, the substituent includes multiple occurrences of amide groups, and each occurrence of an amide group is separated from the carbon of the pyrazine ring to which the substituent is bonded by at least two atoms. In other words, in these embodiments, no portion of an amide group is located within two atoms of the carbon (of the pyrazine ring) to which the substituent is bonded. In some substituents that include multiple occurrences of amide groups, each occurrence of an amide group may be separated from the carbon of the pyrazine ring to which the substituent is bonded by at least three, at least four, at least five, or even at least six atoms.

Still referring to the fourth aspect, in some embodiments, each of the four carbons of the pyrazine ring has a substituent bonded thereto. In such embodiments, each occurrence of an amide group of any of the four substituents may be separated from the carbon of the pyrazine ring to which the substituent is bonded by at least two atoms. In other embodiments, each occurrence of an amide of any of the four substituents may be separated from the carbon of the pyrazine ring to which the substituent is bonded by at least three, at least four, at least five, or even at least six atoms.

In pyrazine derivatives of the fourth aspect, the substituent(s) may include any of a number of other appropriate groups besides at least one amide. For instance, in some embodiments, the substituent that includes the amide may also include at least one PEG unit (e.g., a plurality of PEG units). In some embodiments, each of a plurality (e.g., two, three, or four) of substituents, each of which is bound to a different carbon of the pyrazine ring, may include at least one PEG unit. For example, in some embodiments, a first substituent bound to a first carbon of the pyrazine ring may include an amide and plurality of PEG units, and a second substituent bound to a second carbon of the pyrazine ring may also include an amide and a plurality of PEG units. In such embodiments, the first and second carbons may be either meta or para to each other.

Still a fifth aspect of the invention is directed to pyrazine derivatives of Formulas I and II below.

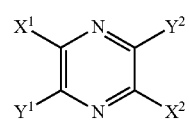

Formula I

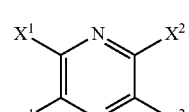

Formula II

With regard to Formulas I and II, each of $X^1$ and $X^2$ is independently $-CO_2R^1$, $-COR^2$, $-SOR^3$, $-SO_2R^4$, $-SO_2OR^5$, $-PO_3R^6R^8$, or $-CONR^7R^9$. Each of $R^1$ to $R^7$ is independently $-(CH_2)_a(CH_2CH_2O)_b(CH_2)_cNR^{10}CONR^{11}(CH_2)_d(CH_2CH_2O)_eR^{20}$, $-(CH_2)_a(CH_2CH_2O)_b(CH_2)_cNR^{12}CSNR^{13}(CH_2)_d(CH_2CH_2O)_eR^{21}$, $-(CH_2)_a(CH_2CH_2O)_b(CH_2)_cCONR^{14}(CH_2)_d(CH_2CH_2O)_eR^{22}$, $-(CH_2)_a(CH_2CH_2O)_b(CH_2)_cNR^{15}SO_2(CH_2)_d(CH_2CH_2O)_eR^{23}$, $-(CH_2)_a(CH_2CH_2O)_b(CH_2)_cSO_2NR^{16}(CH_2)_d(CH_2CH_2O)_eR^{24}$, $-(CH_2)_a(CH_2CH_2O)_b(CH_2)_cNR^{17}CO(CH_2)_d(CH_2CH_2O)_eR^{25}$, $-(CH_2)_a(CH_2CH_2O)_b(CH_2)_cNR^{18}CO_2(CH_2)_d(CH_2CH_2O)_eR^{26}$, $-(CH_2)_a(CH_2CH_2O)_b(CH_2)_cOC(O)NR^{19}(CH_2)_d(CH_2CH_2O)_eR^{27}$, or any combination thereof. Each of $R^8$ to $R^{19}$ is independently $-H$ or $-CH_3$. Each of $R^{20}$ to $R^{27}$ is independently $-H$, $-CH_3$, $-(CH_2)_fNR^{28}C(O)NR^{29}(CH_2)_g(CH_2CH_2O)_hR^{38}$, $-(CH_2)_fNR^{30}CSNR^{31}(CH_2)_g(CH_2CH_2O)_hR^{39}$, $-(CH_2)_f(O)NR^{32}(CH_2)_g(CH_2CH_2O)_hR^{40}$, $-(CH_2)_fS(O)_2NR^{33}(CH_2)_g(CH_2CH_2O)_hR^{41}$, $-(CH_2)_fNR^{34}S(O)_2(CH_2)_g(CH_2CH_2O)_hR^{42}$, $-(CH_2)_fNR^{30}C(O)(CH_2)_g(CH_2CH_2O)_hR^{43}$, $-(CH_2)_fNR^{36}C(O)O(CH_2)_g(CH_2CH_2O)_hR^{44}$, $-(CH_2)_fOC(O)NR^{37}(CH_2)_g(CH_2CH_2O)_hR^{45}$, $-CO(AA)$, $-CONH(PS)$, or any combination thereof. Each of $R^{28}$ to $R^{37}$ is independently $-H$ or $-CH_3$. Each of $R^{38}$ to $R^{45}$ is independently $-H$, $-CH_3$, $-CO(AA)$ or $-CONH(PS)$.

Still referring to pyrazine derivatives of Formulas I and II above, each of $Y^1$ and $Y^2$ is independently $-OR^{46}$, $-SR^{47}$, $-NR^{48}R^{49}$, $-N(R^{50})COR^{51}$, $-P(R^{52})_3$, $-P(OR^{53})_3$, or

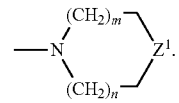

$Z^1$ is a single bond, $-CR^{54}R^{55}$, $-O$, $-NR^{56}$, $-NCOR^{57}$, $-S$, $-SO$, or $-SO_2$. Each of $R^{46}$ to $R^{57}$ is independently $-H$, $-(CH_2)_cOR^{68}$, $-CH_2(CHOH)_cR^{69}$, $-CH_2(CHOH)_cCO_2H$, $-(CHCO_2H)_cCO_2H$, $-(CH_2)_cNR^{70}R^{71}$, $-CH[(CH_2)_fNH_2]_cCO_2H$, $-CH[(CH_2)_fNH_2]_cCH_2OH$, $-CH_2(CHNH_2)_cCH_2NR^{72}R^{73}$, $-(CH_2CH_2O)_eR^{74}$, $-(CH_2)_cCO(CH_2CH_2O)_eR^{75}$, $-(CH_2)_i(CH_2CH_2O)_j(CH_2)_kNR^{58}C(O)NR^{59}(CH_2)_i(CH_2CH_2O)_oR^{76}$, $-(CH_2)_i(CH_2CH_2O)_j(CH_2)_kNR^{60}C(S)NR^{61}(CH_2)_i(CH_2CH_2O)_oR^{77}$, $-(CH_2)_i(CH_2CH_2O)_j(CH_2)_kC(O)NR^{62}(CH_2)_i(CH_2CH_2O)R^{78}$, $-(CH_2)_i(CH_2CH_2O)_j(CH_2)_kS(O)_2NR^{63}(CH_2)_i(CH_2CH_2O)_oR^{79}$, $-(CH_2)_i(CH_2CH_2O)_j(CH_2)_kNR^{64}S(O)_2(CH_2)_i(CH_2CH_2O)_oR^{80}$, $-(CH_2)_i(CH_2CH_2O)_j(CH_2)_kNR^{65}C(O)(CH_2)_i(CH_2CH_2O)_oR^{81}$, $-(CH_2)_i(CH_2CH_2O)_j(CH_2)_kOC(O)O(CH_2)_i(CH_2CH_2O)_oR^{82}$, $-(CH_2)_i(CH_2$ $CH_2O)_j(CH_2)_kOC(O)NR^{67}(CH_2)_l(CH_2CH_2O)OR^{83}$, $—(CH_2)_aSO_3H$, $—(CH_2)_aSO_3^-$, $—(CH_2)_aOSO_3H$, $—(CH_2)_aOSO_3^-$, $—(CH_2)_aNHSO_3H$, $—(CH_2)_aNHSO_3^-$, $—(CH_2)_aPO_3H_2$, $—(CH_2)_aPO_3H^-$, $—(CH_2)_aPO_3^=$, $—(CH_2)_aOPO_3H_2$, $—(CH_2)_aOPO_3H^-$, $—(CH_2)_aOPO_3$, or any combination thereof. Each of $R^{58}$ to $R^{67}$ is independently —H or —$CH_3$. Each of $R^{68}$ to $R^{83}$ is independently —H, —$CH_3$, $—(CH_2)_pNR^{81}C(O)NR^{82}(CH_2)_q(CH_2CH_2O)_sR^{77}$, $—(CH_2)_pC(O)NR^{83}(CH_2)_q(CH_2CH_2O)_sR^{79}$, $—(CH_2)_pS(O)_2NR^{84}(CH_2)_q(CH_2CH_2O)_sR^{81}$, $—(CH_2)_pN^{85}S(O)_2(CH_2)_q(CH_2CH_2O)_sR^{83}$, $—(CH_2)_pNR^{86}C(O)(CH_2)_q(CH_2CH_2O)_sR^{85}$, $—(CH_2)_pNR^{86}C(O)O(CH_2)_q(CH_2CH_2O)_sR^{87}$, $—(CH_2)_pOC(O)NR^{88}(CH_2)_q(CH_2CH_2O)_sR^{89}$, or any combination thereof. Each of $R^{81}$ to $R^{89}$ is independently —H or —$CH_3$.

(AA) is a polypeptide chain that includes one or more natural or unnatural α-amino acids linked together by peptide bonds. Moreover, (PS) is a sulfated or non-sulfated polysaccharide chain comprising one or more monosaccharide units connected by glycosidic linkages.

Still referring to pyrazine derivatives of Formulas I and II, each of 'a', 'd', 'g', 'i', 'l', and 'q' is independently 0, 1, 2, 3, 4, 5, 6, 7, 8, 9 or 10. In addition, each of 'c', 'f', 'k', and 'p' is independently 1, 2, 3, 4, 5, 6, 7, 8, 9 or 10. Each of 'b' and 'j' is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100. Further, each of 'e', 'h', 'o', and 's' is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In addition, each of 'm' and 'n' is independently 1, 2 or 3.

With regard to pyrazine derivatives of the fifth aspect, each of $X^1$ and $X^2$ may independently be —$CO_2R^1$, —$COR^2$, or —$CONR^7R^9$ in some embodiments. In other embodiments, each of $X^1$ and $X^2$ may independently be —$CO_2R'$ or —$CONR^7R^9$.

$Y^1$ and $Y^2$ may independently be —$NR^{48}R^{49}$ or

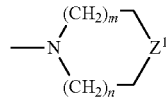

in some embodiments. For instance, in some embodiments each of $Y^1$ and $Y^2$ is —$NR^{48}R^{49}$.

In some embodiments, $Z^1$ may be —O, —$NR^{56}$, —S, —SO or —$SO_2$. For instance, in some embodiments, $Z^1$ may be —O or —$NR^{56}$.

In some embodiments, each of $R^1$ to $R^7$ may independently be $—(CH_2)_aNR^{10}CONR^{11}(CH_2)_b(CH_2CH_2O)CR^{20}$, $—(CH_2)_aCONR^{14}(CH_2)_b(CH_2CH_2O)_eR^{22}$, $—(CH_2)_aSO_2NR^{15}(CH_2)_b(CH_2CH_2O)CR^{23}$, $—(CH_2)_aSO_2NR^{16}(CH_2)_b(CH_2CH_2O)_cR^{24}$, $—(CH_2)_aNR^{17}CO(CH_2)_b(CH_2CH_2O)_cR^{25}$, $—(CH_2)_aNR^{18}CO_2(CH_2)_b(CH_2CH_2O)_cR^{26}$, or $—(CH_2)_aOC(O)NR^{19}(CH_2)_b(CH_2CH_2O)_cR^{27}$. For instance, in some embodiments, each of $R^1$ to $R^6$ may be $—(CH_2)_aNR^{10}CONR^{11}(CH_2)_b(CH_2CH_2O)CR^{20}$. In other embodiments, each of $R^1$ to $R^7$ may independently be $—(CH_2)_a(CH_2CH_2O)_b(CH_2)_cNR^{12}CSNR^{13}(CH_2)_d(CH_2CH_2O)_eR^{21}$, $—(CH_2)_f(CH_2CH_2O)_b(CH_2)_cCONR^{14}(CH_2)_d(CH_2CH_2O)_eR^{22}$, $—(CH_2)_a(CH_2CH_2O)_b(CH_2)_cNR^{15}SO_2(CH_2)_d(CH_2CH_2O)_eR^{23}$, $—(CH_2)_a(CH_2CH_2O)_b(CH_2)_cSO_2NR^{16}(CH_2)_d(CH_2CH_2O)_eR^{24}$, $—(CH_2)_a(CH_2CH_2O)_b(CH_2)_cNR^{18}CO_2(CH_2)_d(CH_2CH_2O)_eR^{26}$, or $—(CH_2)_a(CH_2CH_2O)_b(CH_2)_cOC(O)NR^{19}(CH_2)_d(CH_2CH_2O)_eR^{27}$.

In some embodiments, each of $R^{20}$ to $R^{27}$ may independently be —H, —$CH_3$, $—(CH_2)_fNR^{30}CSNR^{31}(CH_2)_g(CH_2CH_2O)_hR^{39}$, $—(CH_2)_fC(O)NR^{32}(CH_2)_g(CH_2CH_2O)_hR^{40}$, $—(CH_2)_fS(O)_2NR^{33}(CH_2)_g(CH_2CH_2O)_hR^{41}$, $—(CH_2)_fNR^{34}S(O)_2(CH_2)_g(CH_2CH_2O)_hR^{42}$, $—(CH_2)_fNR^{36}C(O)O(CH_2)_g(CH_2CH_2O)_hR^{44}$, $—(CH_2)_fOC(O)NR^{37}(CH_2)_f(CH_2CH_2O)_hR^{45}$, —CO(AA), or CONH(PS).

In some embodiments, each of $R^{31}$ to $R^{45}$ may independently be —H or —$CH_3$.

In some embodiments, $R^{46}$ to $R^{57}$ may independently be —H, $—(CH_2)_cOR^{68}$, $—CH_2(CHOH)_cR^{69}$, $—CH_2(CHOH)_cCO_2H$, $—(CHCO_2H)_cCO_2H$, $—(CH_2)_cNR^{70}R^{71}$, $—CH[(CH_2)_fNH_2]_cCO_2H$, $—CH[(CH_2)_fNH_2]_cCH_2OH$, $—CH_2(CHNH_2)_cCH_2N^{72}R^{73}$, $—(CH_2CH_2O)_eR^{74}$, $—(CH_2)_cCO(CH_2CH_2O)_eR^{75}$, $—(CH_2)_f(CH_2CH_2O)_j(CH_2)_kR^{58}C(O)NR^{59}(CH_2)_l(CH_2CH_2O)_oR^{76}$, $—(CH_2)_i(CH_2CH_2O)_j(CH_2)_kNR^{60}C(S)NR^{61}(CH_2)_l(CH_2CH_2O)R^{77}$, $—(CH_2)_i(CH_2CH_2O)_j(CH_2)_kC(O)NR^{62}(CH_2)_l(CH_2CH_2O)_oR^{78}$, $—(CH_2)_i(CH_2CH_2O)_j(CH_2)_kS(O)_2NR^{63}(CH_2)_l(CH_2CH_2O)_oR^{79}$, $—(CH_2)_i(CH_2CH_2O)_j(CH_2)_kNR^{64}S(O)_2(CH_2)_l(CH_2CH_2O)_oR^{80}$, $—(CH_2)_i(CH_2CH_2O)_j(CH_2)_kNR^{65}C(O)(CH_2)_l(CH_2CH_2O)_oR^{81}$, $—(CH_2)_i(CH_2CH_2O)_j(CH_2)_kN^{66}C(O)O(CH_2)_l(CH_2CH_2O)_oR^{82}$, $—(CH_2)_i(CH_2CH_2O)_j(CH_2)_kOC(O)N^{67}(CH_2)_l(CH_2CH_2O)_oR^{83}$, $—(CH_2)_aSO_3H$, $—(CH_2)_aSO_3^-$, $—(CH_2)_aOSO_3H$, $—(CH_2)_aOSO_3^-$, $—(CH_2)_aNHSO_3H$, or $—(CH_2)_aNHSO_3^-$.

As stated above, (AA) is polypeptide chain including one or more natural or unnatural α-amino acids linked together by peptide bonds. The polypeptide chain (AA) may be a homopolypeptide chain or a heteropolypeptide chain, and may be any appropriate length. For instance, in some embodiments, the polypeptide chain may include 1 to 100 α-amino acid(s), 1 to 90 α-amino acid(s), 1 to 80 α-amino acid(s), 1 to 70 α-amino acid(s), 1 to 60 α-amino acid(s), 1 to 50 α-amino acid(s), 1 to 40 α-amino acid(s), 1 to 30 α-amino acid(s), 1 to 20 α-amino acid(s), or even 1 to 10 α-amino acid(s). In some embodiments, the α-amino acids of the polypeptide chain (AA) are selected from aspartic acid, asparigine, arginine, histidine, lysine, glutamic acid, glutamine, serine, and homoserine. In some embodiments, the α-amino acids of the polypeptide chain (AA) are selected from aspartic acid, glutamic acid, serine, and homoserine. In some embodiments, the polypeptide chain (AA) refers to a single amino (e.g., either aspartic acid or serine).

As stated above, (PS) is a sulfated or non-sulfated polysaccharide chain including one or more monosaccharide units connected by glycosidic linkages. The polysaccharide chain (PS) may be any appropriate length. For instance, in some embodiments, the polysaccharide chain may include 1 to 100 monosaccharide unit(s), 1 to 90 monosaccharide unit(s), 1 to 80 monosaccharide unit(s), 1 to 70 monosaccharide unit(s), 1 to 60 monosaccharide unit(s), 1 to 50 monosaccharide unit(s), 1 to 40 monosaccharide unit(s), 1 to 30 monosaccharide unit(s), 1 to 20 monosaccharide unit(s), or even 1 to 10 monosaccharide unit(s). In some embodiments, the polysaccharide chain (PS) is a homopolysaccharide chain consisting of either pentose or hexose monosaccharide units. In other embodiments, the polysaccharide chain (PS) is a heteropolysaccharide chain consisting of one or both pentose and hexose monosaccharide units. In some embodiments, the monosaccharide units of the polysaccharide chain (PS) are selected from the group consisting of glucose, fructose, mannose, xylose and ribose. In some embodiments, the polysaccharide chain (PS) refers to a single monosaccharide unit (e.g., either glucose or fructose).

Still referring to pyrazine derivatives of Formulas I and II, in some embodiments, each of 'a', 'd', 'g', 'i', and 'q' may independently be 1, 2, 3, 4, 5 or 6. Each of 'e', 'h', 'o', and 's' may independently be 1, 2, 3, 4, 5, 6, 7, 8, 9, 10, 11, 12, 13, 14, 15, 16, 17, 18, 19 or 20 in some embodiments. Similarly, in some embodiments, each of 'b' and 'j' may independently be 0, 1, 2, 3, 4, 5, 6, 7, 8, 9, 10, 11, 12, 13, 14, 15, 16, 17, 18, 19 or 20. In some embodiments, each of 'm' and 'n' may independently be 1 or 2.

Any of the pyrazine derivatives described above may exhibit any appropriate molecular weight. For instance, in some embodiments, a pyrazine derivative of the invention may have a molecular weight of no more than about 20000. In other embodiments, a pyrazine derivative of the invention may have a molecular weight of no more than about 15000, 14000, 13000, 12000, 11000, 10000, 9000, 8000, 7000, 6000, 5000, 4500, 4000, 3500, 3000, 2500, 2000, 1500, 1000, 900, 800, 700, 600, 500, 400, 300, 200, or even 100. Other embodiments may have molecular weights that are greater than about 20000.

Yet a sixth aspect of the invention is directed to methods of using pyrazine derivatives described herein. In such methods, a pyrazine derivative is administered to a patient and utilized in a medical photodiagnostic and/or imaging procedure (e.g., assessing renal function).

Still a seventh aspect of the invention is directed to pharmaceutically acceptable compositions, each of which includes one or more pyrazine derivatives disclosed herein. The phrase "pharmaceutically acceptable" herein refers substances that are, within the scope of sound medical judgment, suitable for use in contact with relevant tissues of humans and animals without undue toxicity, irritation, allergic response and the like, and are commensurate with a reasonable benefit/risk ratio. The compositions of this seventh aspect may include one or more appropriate excipients such as, but not limited to, suitable diluents, preservatives, solubilizers, emulsifiers, adjuvant and/or carriers. One example of a composition of this aspect may include at least one pyrazine derivative of Formula I and/or at least one pyrazine derivative of Formula II.

Yet an eighth aspect of the invention is directed to methods of determining renal function using pyrazine derivatives such as those described above (e.g., with regard to Formulas I and II). In these methods, an effective amount of a pyrazine derivative is administered into the body of a patient (e.g., a mammal such as a human or animal subject). Incidentally, an "effective amount" herein generally refers to an amount of pyrazine derivative that is sufficient to enable renal clearance to be analyzed. The pyrazine derivative in the body of the patient is exposed to at least one of visible and near infrared light. Due to this exposure of the pyrazine derivative to the visible and/or infrared light, the pyrazine derivative emanates spectral energy that may be detected by appropriate detection equipment. This spectral energy emanating from the pyrazine derivative may be detected using an appropriate detection mechanism such as an invasive or non-invasive optical probe. Herein, "emanating" or the like refers to spectral energy that is emitted and/or fluoresced from a pyrazine derivative. Renal function may be determined based on the spectral energy that is detected. For example, an initial amount of the amount of pyrazine derivative present in the body of a patient may be determined by a magnitude/intensity of light emanated from the pyrazine derivative that is detected (e.g., in the bloodstream). As the pyrazine derivative is cleared from the body, the magnitude/intensity of detected light generally diminishes. Accordingly, a rate at which this magnitude of detected light diminishes may be correlated to a renal clearance rate of the patient. This detection may be done periodically or in substantially real time (providing a substantially continuous monitoring of renal function). Indeed, methods of the present invention enable renal function/clearance to be determined via detecting one or both a change and a rate of change of the detected magnitude of spectral energy (indicative of an amount of the pyrazine derivative that has not been cleared) from the portion of the pyrazine derivative that remains in the body. While this aspect has been described with regard to use of a single pyrazine derivative of the invention, it should be noted that some embodiments of this aspect include the use of compositions of the invention that may include one or more pyrazine derivatives disclosed herein.

Yet a ninth aspect of the invention is directed to a method for producing pyrazine derivatives. In this method, an aminopyrazine compound and a carbonyl compound are combined in the presence of a reducing agent.

In some embodiments of the method, the aminopyrazine compound is a diaminopyrazine, and the pyrazine derivative is an N,N'-alkylated diaminopyrazine.

Some embodiments of the method may include the aminopyrazine compound, the carbonyl compound, and a solvent being combined in the presence of the reducing agent.

In some embodiments of the method, the aminopyrazine compound and a carbonyl compound may be combined at a temperature between about −20° and about 50° C. For instance, in some embodiments, this combining may occur at a temperature between about −5° and about 30° C.

The carbonyl compound used in the method may be any appropriate carbonyl compound. For instance, in some embodiments, the carbonyl compound may be of Formula III below.

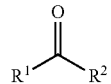

Formula III

In Formula III, each of $R^1$ and $R^2$ is independently hydrogen, $C_1$-$C_{10}$ alkyl, $C_5$-$C_{20}$ aralkyl, $C_1$-$C_{20}$ hydroxyalkyl, $C_2$-$C_{20}$ polyhydroxyalkyl, $-(CH_2)_n CO_2 R^3$, $-(CH_2 CH_2 O)_m R^4$, or mono- or poly-saccharide containing 1 to 50 units.

Referring to $R^1$ and $R^2$ of Formula III, m and n may be any appropriate integers. For instance, in some embodiments, each of m and n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In some embodiments, each of m and n may independently be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In other embodiments, m and n may independently be 1, 2, 3, 4, 5, 6, 7, 8, 9, 10, 11, 12, 13, 14, 15, 16, 17, 18, 19 or 20. In yet other embodiments, m and n may independently be 1, 2, 3, 4, 5, 6, 7, 8, 9 or 10.

Still referring to $R^1$ and $R^2$ of Formula III, each occurrence of $R^3$ and $R^4$ is independently hydrogen, $C_1$-$C_{10}$ alkyl, $C_5$-$C_{20}$ aralkyl, $C_1$-$C_{10}$ acyl, $C_1$-$C_{20}$ hydroxyalkyl, $C_2$-$C_{20}$ polyhydroxyalkyl, or mono- or poly-saccharide containing 1 to 50 units. For instance, in some embodiments, each of $R^3$ and $R^4$ is independently hydrogen, $C_1$-$C_{10}$ alkyl, $C_1$-$C_{20}$ hydroxyalkyl, or $C_2$-$C_{20}$ polyhydroxyalkyl.

The aminopyrazine compound utilized in the method may be any appropriate aminopyrazine compound. For instance, the aminopyrazine compound utilized may be a compound of the following Formula IV or V below.

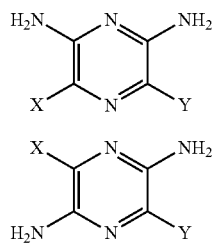

Formula IV

Formula V

With regard to Formulas IV and V above, each X and Y is independently hydrogen, $C_1$-$C_{10}$ alkyl, —$OR^5$, —$SR^6$, —$NR^7R^8$, —$N(R^9)COR^{10}$, halo, trihaloakyl, —CN, —$NO_2$, —CO—Z—$R^{11}$, —$SOR^{12}$, —$SO_2R^{13}$, —$SO_2OR^{14}$, or —$PO_3R^{15}R^{16}$. Z is a single bond, —O—, —$NR^{17}$—, —NH($CH_2$)$_p$NH—, —NH($CH_2$)$_p$O—, —NH($CH_2$)$_p$CO—, —NH($CH_2$)$_p$NHCO—, —NH($CH_2$)$_p$CONH—, —NH($CH_2$)$_p$NHCONH—, —NH($CH_2$)$_p$NHCSNH—, or —NH($CH_2$)$_p$NHCO$_2$—. Each of $R^5$ to $R^{17}$ is independently hydrogen, $C_1$-$C_{10}$ alkyl, $C_5$-$C_{20}$ aralkyl, $C_1$-$C_{10}$ acyl, $C_1$-$C_{20}$ hydroxyalkyl, $C_2$-$C_{20}$ polyhydroxyalkyl, —($CH_2CH_2O$)$_q R^8$, or mono- or poly-saccharide containing 1 to 50 units. $R^{18}$ is hydrogen, $C_1$-$C_{10}$ alkyl, $C_5$-$C_{20}$ aralkyl, $C_1$-$C_{10}$ acyl, $C_1$-$C_{20}$ hydroxyalkyl, $C_2$-$C_{20}$ polyhydroxyalkyl, or mono- or poly-saccharide containing 1 to 50 units. The integer p 0, 1, 2, 3, 4, 5 or 6. Further, the integer q is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50.

In some compounds of Formulas IV and V above, each of X and Y may be —CN in some embodiments and —CO—Z—$R^{11}$ in other embodiments. In embodiments of compounds of Formulas IV and V that include $R^{11}$, $R^{11}$ of some embodiments may be hydrogen, $C_1$-$C_{10}$ alkyl, $C_1$-$C_{20}$ hydroxyalkyl, or $C_2$-$C_{20}$ polyhydroxyalkyl. When each of X and Y is —CO—Z—$R^{11}$, Z may be —$NR^{17}$— in some embodiments, —NH($CH_2$)$_p$— in other embodiments, and —NH($CH_2$)$_p$CO— in other embodiments. In the case that Z is —$NR^{17}$—, $R^{17}$ of some embodiments may be hydrogen or $C_1$-$C_{10}$ alkyl. In the case that Z is either NH($CH_2$)$_p$NH— or —NH($CH_2$)$_p$CO—, the integer p of some embodiments may be 0, 1, 2, 3 or 4.

The reducing agent utilized in the method may be any appropriate reducing agent. For instance, in some embodiments, the reducing agent is ammonium formate, diimide, Zn/HCl, sodium triacetoxyborohydride, sodium borohydride, pyridine/borane, lithium aluminium hydride, lithium borohydride, sodium cyanoborohydride, sodium amalgam, $H_2$/Pd/C, $H_2$/Pt/C, $H_2$/Rh/C, $H_2$/Raney® Nickel, or any combination thereof. In some embodiments, the reducing agent includes or is sodium triacetoxyborohydride. In some embodiments, the reducing agent includes or is sodium cyanoborohydride.

In the case that a solvent is utilized in the method, the solvent may be any appropriate solvent such as, for example, water, $C_1$-$C_8$ alcohol, $C_1$-$C_8$ ether, $C_1$-$C_8$ ester, dimethyl formamide, dimethyl acetamide, acetic acid, trifluoroacetic acid, dimethyl sulfoxide, or any combination thereof. In some embodiments, the solvent may be methanol, ethanol, isopropyl alcohol, tetrahydrofuran, dioxane, glyme, dimethyl formamide, dimethyl sulfoxide, or any combination thereof.

A related area of the present invention is directed pyrazine derivatives that are made utilizing a method described herein. Pyrazine derivatives made using the method described herein may be utilized in a number of appropriate processes and procedures (e.g., medical procedures). For instance, pyrazine derivatives made using a method described herein may be utilized in assessing renal function of a medical patient and/or as intermediates in processes for manufacturing pyrazine derivatives and/or compositions that include pyrazine derivatives (e.g., for use in assessing renal function of medical patients).

These and other features, aspects and advantages of the present teachings will become better understood with reference to the following description, examples and appended claims.

Those of skill in the art will understand that the drawings, described below, are for illustrative purposes only. The drawings are not intended to limit the scope of the present teachings in any way.

DETAILED DESCRIPTION OF SPECIFIC EMBODIMENTS

Abbreviations and Definitions

Figure 1:
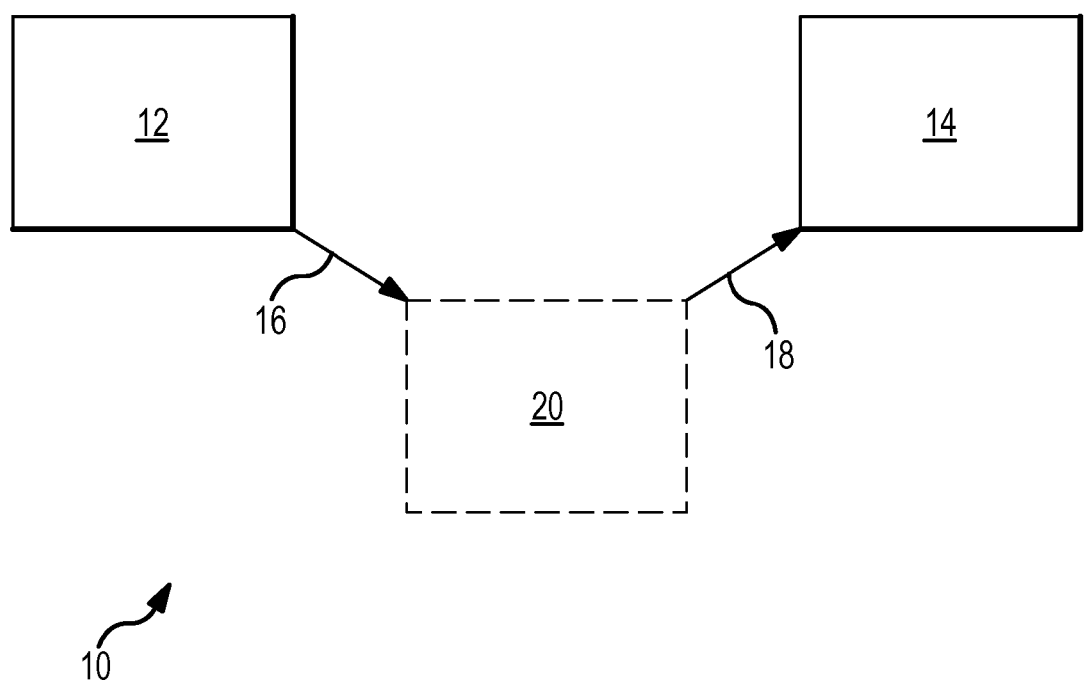
FIG. 1. A block diagram of an assembly for assessing renal function.

To facilitate understanding of the invention, a number of terms and abbreviations as used herein are defined below as follows:

Pharmacokinetic: As used herein, the term "pharmacokinetic" refers to how a compound is absorbed, distributed, metabolized, and eliminated by the body.

Half-life: As used herein, the term "half-life" refers to the time required for the amount of a compound in the body to fall by half.

Clearance: As used herein, the term "clearance" describes the efficiency of elimination of a compound from the body.

A, An, and The: As used herein, the articles "a", "an", and "the" are intended to mean that there are one or more of something that the article(s) introduce(s).

Comprising, Including, and Having: As used herein, the terms "comprising", "including", and "having" are intended to be inclusive and mean that there may be additional items (e.g., substituents, groups, elements, steps, etc.) other than that mentioned.

Pyrazine Derivatives, Methods of Using Pyrazine Derivatives, and Preparing Pyrazine Derivatives Pyrazine Derivatives, Methods of Using Pyrazine Derivatives, and Preparing Pyrazine Derivatives The present invention provides compounds that can be detected in vivo and used in a number of medical procedures, including renal function monitoring. The compounds can be pyrazine derivatives having a pyrazine ring that can have a substituent bonded to a carbon of the pyrazine ring. The carbon of the pyrazine ring can have a substituent bonded thereto that includes a group selected from urea, amide, sulfonamide, thiourea, carbamate, or any combination thereof. Without being bound by a particular theory, the pyrazine derivatives of the present invention are designed to be hydrophilic and/or have rigid functionality which it thought to allow for rapid renal clearance while also providing pharmacokinetic properties for monitoring renal function. One of skill in the art will recognize that other uses are contemplated herein. For example, pyrazine derivatives of the present invention can be used in accordance with the methods provided in patent application PCT/US2006/039732, incorporated herein by reference in its entirety.

Molecules absorbing, emitting, and/or scattering in the visible, NIR, and/or long-wavelength (UV-A, >300 nm) region of the electromagnetic spectrum are useful for optical measurement. The high sensitivity associated with fluorescence phenomenon permits quantification without the negative effects of radioactivity or ionizing radiation. Pyrazine derivatives of general structures A and B below are one of the few classes of small molecules having desirable photophysical properties for biomedical optical applications.

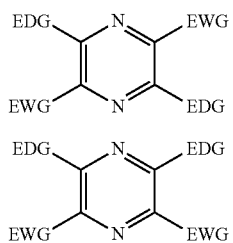

These compounds have low molecular weight fluorescent scaffold systems with surprisingly bright emissions in the yellow-to-red region of the electromagnetic spectrum. In particular, pyrazine derivative A that contains electron donating groups (EDG) in the 2,5 positions and electron withdrawing groups (EWG) in the 3,6 positions are shown to absorb and emit in the visible region with a large Stokes shift.[15-18] These properties allow flexibility in both tuning a molecule to a desired wavelength and introducing a variety of substituents to improve clearance properties.

Molecules designed for renal monitoring applications must be cleared from the body via the kidneys. Hydrophilic, anionic substances are generally capable of being excreted by the kidneys.[19] Renal clearance typically occurs via two pathways: glomerular filtration and tubular secretion. Tubular secretion is characterized as an active transport process, and substances clearing via this pathway exhibit specific properties with respect to size, charge and lipophilicity. Most of the substances that pass through the kidneys are filtered through the glomerulus (a small intertwined group of capillaries in the malpighian body of the kidney). In general, molecules which are highly hydrophilic and small (creatinine, molecular weight=113) to moderately sized (inulin, molecular weight 5500) are rapidly cleared from systemic circulation by glomerular filtration.[20]

In addition to these properties, the ideal GFR agent should not be reabsorbed nor secreted by the renal tubule, exhibit negligible binding to plasma proteins, and have very low toxicity. Optical probes that satisfy all of these requirements strike a balance between photophysical properties and the molecular size and hydrophilicity of the compound.

To achieve these goals, polyethylene glycol (PEG) units can be incorporated with the pyrazine core. As referred to herein, a "PEG unit" means a $CH_2CH_2O$ unit. PEG units are typically components of highly soluble oligomers and polymers of ethylene glycol. Further, they tend to be highly biocompatible, non-immunogenic, and non-toxic. PEG polymers have been used primarily to modify therapeutic proteins for enhancement of their pharmacokinetic performance in vivo. PEG polymers are usually of high molecular weight (20-500 kDal) and may be branched or linear chains. Pegylation is known to significantly increase the apparent size (Stokes-Einstein radius or hydrodynamic volume) of the conjugated drug compound. In the case of some therapeutic proteins, the very large hydrodynamic volume of the conjugate has been shown to slow down renal clearance and prolong pharmacokinetic half-life. Ikada has studied the biodistribution of PEG polymers after i.v. administration and found that the terminal half-life in the circulation extended from 18 min to 1 day as the PEG molecular weight increased from 6,000 to 190,000.[21] The lower end of this range is acceptable for a renal function agent. Lower molecular weight PEG polymers (at least <6,000) are known to be filtered by the glomerulus and not reabsorbed by the renal tubules.[21]

Additionally, inserting rigidifying functional groups between the PEG units can further improve the pharmacokinetic performance of the renal monitoring agents. These rigidifying groups include urea, amide, sulfonamide, thiourea, carbamate, or any combination thereof. Such groups are good hydrogen bond donors and acceptors and have partial double bond character which restricts free rotation about the bond and confers a planar geometry to the functional group. Without being bound by a particular theory, it is believed that these rigid groups enhance the pharmacokinetic properties of the renal agents by increasing the apparent volume and modulating aggregation of the resulting pyrazine derivatives.

In one aspect of the present invention, pyrazine derivatives can have at least one occurrence of a urea, amide, sulfonamide, thiourea, carbamate, or any combination thereof. This "occurrence" is typically separated from the carbon of the pyrazine ring to which the substituent is bonded by at least two atoms. For example, the substituent may include one of the aforementioned groups that is bonded directly to the carbon as long as the substituent also has at least one occurrence of one of the aforementioned groups that is separated from the carbon of the pyrazine ring to which the substituent is bonded by at least two atoms.

The occurrence of the urea, amide, sulfonamide, thiourea, carbamate, or any combination thereof, may be separated from the carbon of the pyrazine ring to which the substituent is bonded by other appropriate atom spacings. For instance, at least one occurrence of the substituent group can be separated from the carbon of the pyrazine ring to which the substituent is bonded by at least three atoms. In other embodiments, at least one occurrence of an aforementioned group can be separated from the carbon of the pyrazine ring to which the substituent is bonded by at least four atoms. In still other embodiments, at least one occurrence of an aforementioned group can be separated from the carbon of the pyrazine ring to which the substituent is bonded by at least five atoms. In other embodiments, at least one occurrence of an aforementioned group can be separated from the carbon of the pyrazine ring to which the substituent is bonded by at least six atoms.

In some embodiments, each occurrence of any of the listed groups may be separated from the carbon of the pyrazine ring to which the substituent is bonded by at least two atoms. In other words, no portion of a urea, amide, sulfonamide, thiourea, carbamate, or any combination thereof is located within two atoms of the carbon of the pyrazine ring to which the substituent is bonded in these embodiments. In some of these embodiments, each occurrence of the group may be separated from the carbon of the pyrazine ring to which the substituent is bonded by at least three, at least four, at least five, or at least six atoms.

In some embodiments, each of the four carbons of the pyrazine ring has a substituent bonded thereto. In such embodiments, each occurrence of any of the listed groups that is a component of one or more of the four substituents may be separated from the carbon of the pyrazine ring to which the substituent is bonded by at least two atoms. In other embodiments, each occurrence of an aforementioned group of any of the four substituents may be separated from the carbon of the pyrazine ring to which the substituent is bonded by at least three, at least four, at least five, or even at least six atoms.

In some embodiments, a first carbon of the pyrazine ring has a first substituent bonded thereto that includes a first group selected from urea, amide, sulfonamide, thiourea, carbamate, and any combination thereof. Further, a second carbon of the pyrazine ring has a second substituent bonded thereto that includes a second group selected from urea, amide, sulfonamide, thiourea, carbamate, and any combination thereof. In such embodiments, the first group is separated from the first carbon of the pyrazine ring by at least two atoms, and the second group is separated from the second carbon of the pyrazine ring by at least two atoms. The first group may be the same as or different from the second group. For instance, in the case that the first group is the same as the second group, the first group and the second may each be an amide. As another example, the first group and the second group may each be a urea. In some embodiments, the first substituent that is bonded to the first carbon of the pyrazine ring may be the same as or different from the second substituent. The first carbon and the second carbon may be located in any appropriate positions along the pyrazine ring. For instance, in some embodiments, the first carbon of the pyrazine ring is para to the second carbon of the pyrazine ring. In other embodiments, the first carbon of the pyrazine ring is meta to the second carbon of the pyrazine ring.

In embodiments having a first substituent that is bonded to a first carbon of the pyrazine ring and a second substituent that is bonded to a second carbon of the pyrazine ring, the first and second substituents may include any of a number of other appropriate groups besides each including at least one of the groups mentioned above (e.g., urea, amide, sulfonamide, thiourea, carbamate, and/or any combination thereof). For instance, in some embodiments, at least one of the first and second substituents may include at least one PEG unit (e.g., a plurality of PEG units). In some embodiments, each of the first substituent and second substituent comprises at least one PEG unit. For example, the first substituent may include a plurality of PEG units, and the second substituent may also include a plurality of PEG units.

Another aspect of the invention is directed to pyrazine derivatives, each of which includes a pyrazine ring that comprises a first carbon, a second carbon, a third carbon, and a fourth carbon. The first carbon has a first substituent bonded thereto, the second carbon has a second substituent bonded thereto, the third carbon has a third substituent bonded thereto, and the fourth carbon has a fourth substituent bonded thereto. Each of the first, second, third, and fourth substituents includes a urea, amide, sulfonamide, thiourea, carbamate, or any combination thereof.

In some embodiments, the structure of a given substituent may be the same as or different from one or more other substituents of the pyrazine derivative. For instance, in some embodiments, the first and second substituents are the same, and the third and fourth substituents are the same but different from the first and second substituents. In such embodiments, the first and second carbons may be para to each other (which means the third and fourth carbons would also be para to each other), or the first and second carbons may be meta to each other (which means the third and fourth carbons would also be meta to each other).

In some embodiments, each of the first substituent and second substituent includes an amide. For instance, each of the first, second, third, and fourth substituents includes an amide.

The pyrazine derivative can include at least two of the first, second, third, and fourth substituents having at least one PEG unit. For instance, each of the first and second substituents can include at least one PEG unit (e.g., a plurality of PEG units). As another example, each of the first, second, third, and fourth substituents can include at least one PEG unit (e.g., a plurality of PEG units).

In yet another aspect of the present invention, a pyrazine derivative can include a pyrazine ring in which a carbon of the pyrazine ring has a substituent bonded thereto that includes a urea group. The urea group is separated from the carbon of the pyrazine ring to which the substituent is bonded by at least two atoms. For instance, the substituent may include one urea that is bonded directly to the carbon of the pyrazine ring as long as the substituent also includes at least one other urea that is separated from the carbon of the pyrazine ring to which the substituent is bonded by at least two atoms. As another example, one substituent may include a urea that is bonded directly to one carbon of the pyrazine ring, and another substituent may include another urea that is separated from the respective carbon of the pyrazine ring to which that substituent is bonded by at least two atoms.

In various embodiments, at least one occurrence of a urea group may be separated from the carbon of the pyrazine ring to which the substituent is bonded by other appropriate atom spacings. For instance, in some embodiments, at least one occurrence of a urea group is separated from the carbon of the pyrazine ring to which the corresponding substituent is bonded by at least three atoms. In other embodiments, at least one occurrence of a urea group is separated from the carbon of the pyrazine ring to which the corresponding substituent is bonded by at least four atoms. In still other embodiments, at least one occurrence of a urea group is separated from the carbon of the pyrazine ring to which the corresponding substituent is bonded by at least five atoms. And in even other embodiments, at least one occurrence of a urea group is separated from the carbon of the pyrazine ring to which the corresponding substituent is bonded by at least six atoms.

In some embodiments, the substituent includes multiple occurrences of urea groups, and each occurrence of a urea group is separated from the carbon of the pyrazine ring to which the substituent is bonded by at least two atoms. In other words, in these embodiments, no portion of a urea group is located within two atoms of the carbon (of the pyrazine ring) to which the substituent is bonded. In some substituents that include multiple occurrences of urea groups, each occurrence of a urea group may be separated from the carbon of the pyrazine ring to which the substituent is bonded by at least three, at least four, at least five, or even at least six atoms.

In some embodiments, each of the four carbons of the pyrazine ring has a substituent bonded thereto. In such embodiments, each occurrence of a urea group of any of the four substituents may be separated from the carbon of the pyrazine ring to which the substituent is bonded by at least two atoms. In other embodiments, each occurrence of a urea of any of the four substituents may be separated from the carbon of the pyrazine ring to which the substituent is bonded by at least three, at least four, at least five, or even at least six atoms.

In various embodiments, the substituent(s) may include any of a number of other appropriate groups besides at least one urea. For instance, in some embodiments, the substituent that includes the urea may also include at least one PEG unit (e.g., a plurality of PEG units). In some embodiments, each of a plurality (e.g., two, three, or four) of substituents, each of which is bound to a different carbon of the pyrazine ring, may include at least one PEG unit. For example, in some embodiments, a first substituent bound to a first carbon of the pyrazine ring may include a urea and plurality of PEG units, and a second substituent bound to a second carbon of the pyrazine ring may also include a urea and a plurality of PEG units. In such embodiments, the first and second carbons may be either meta or para to each other. In other embodiments, a first substituent bound to a first carbon of the pyrazine ring may include a urea and plurality of PEG units, and a second substituent bound to a second carbon of the pyrazine ring may not include a urea but may include one or more PEG units.

In yet another aspect of the present invention, a carbon of the pyrazine ring has a substituent bonded thereto that includes an amide group. This amide group is separated from the carbon of the pyrazine ring to which the substituent is bonded by at least two atoms. So, for example, the substituent may include one amide that is bonded directly to the carbon of the pyrazine ring as long as the substituent also includes at least one other amide that is separated from the carbon of the pyrazine ring to which the substituent is bonded by at least two atoms. As another example, one substituent may include an amide that is bonded directly to one carbon of the pyrazine ring, and another substituent may include another amide that is separated from the respective carbon of the pyrazine ring to which that substituent is bonded by at least two atoms.

In various embodiments, at least one occurrence of an amide group may be separated from the carbon of the pyrazine ring to which the substituent is bonded by other appropriate atom spacings. For instance, at least one occurrence of an amide group is separated from the carbon of the pyrazine ring to which the corresponding substituent is bonded by at least three atoms. In other embodiments, at least one occurrence of an amide group is separated from the carbon of the pyrazine ring to which the corresponding substituent is bonded by at least four atoms. In still other embodiments, at least one occurrence of an amide group is separated from the carbon of the pyrazine ring to which the corresponding substituent is bonded by at least five atoms. In other embodiments, at least one occurrence of an amide group is separated from the carbon of the pyrazine ring to which the corresponding substituent is bonded by at least six atoms.

In some embodiments, the substituent includes multiple occurrences of amide groups, and each occurrence of an amide group is separated from the carbon of the pyrazine ring to which the substituent is bonded by at least two atoms. In other words, in these embodiments, no portion of an amide group is located within two atoms of the carbon (of the pyrazine ring) to which the substituent is bonded. In some substituents that include multiple occurrences of amide groups, each occurrence of an amide group may be separated from the carbon of the pyrazine ring to which the substituent is bonded by at least three, at least four, at least five, or even at least six atoms.

In some embodiments, each of the four carbons of the pyrazine ring has a substituent bonded thereto. In such embodiments, each occurrence of an amide group of any of the four substituents may be separated from the carbon of the pyrazine ring to which the substituent is bonded by at least two atoms. In other embodiments, each occurrence of an amide of any of the four substituents may be separated from the carbon of the pyrazine ring to which the substituent is bonded by at least three, at least four, at least five, or even at least six atoms.

The substituent(s) may include any of a number of other appropriate groups besides at least one amide. For instance, in some embodiments, the substituent that includes the amide may also include at least one PEG unit (e.g., a plurality of PEG units). In some embodiments, each of a plurality (e.g., two, three, or four) of substituents, each of which is bound to a different carbon of the pyrazine ring, may include at least one PEG unit. For example, in some embodiments, a first substituent bound to a first carbon of the pyrazine ring may include an amide and plurality of PEG units, and a second substituent bound to a second carbon of the pyrazine ring may also include an amide and a plurality of PEG units. In such embodiments, the first and second carbons may be either meta or para to each other. In other embodiments, a first substituent bound to a first carbon of the pyrazine ring may include an amide and plurality of PEG units, and a second substituent bound to a second carbon of the pyrazine ring may not include an amide but may include one or more PEG units.

Yet another aspect of the present invention is directed to pyrazine derivatives of Formulas I and II below.

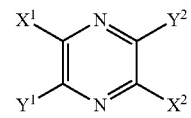

Formula I

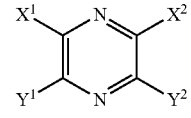

Formula II

With regard to Formulas I and II, each of $X^1$ and $X^2$ can independently be $-CO_2R^1$, $-COR^2$, $-SOR^3$, $-SO_2R^4$, $-SO_2OR^5$, $-PO_3R^6R^8$, or $-CONR^7R^9$. Each of $R^1$ to $R^7$ can independently be $-(CH_2)_a(CH_2CH_2O)_b$ $(CH_2)_cNR^{10}CONR^{11}(CH_2)_d(CH_2CH_2O)_eR^{20}$, $-(CH_2)_a$ $(CH_2CH_2O)_b(CH_2)_cNR^{12}CSNR^{13}(CH_2)_d(CH_2CH_2O)_eR^{21}$, $-(CH_2)_a(CH_2CH_2O)_b(CH_2)_cCONR^{14}(CH_2)_d(CH_2 CH_2O)_eR^{22}$, $-(CH_2)_a(CH_2CH_2O)_b(CH_2)_cNR^{15}SO_2(CH_2)_d (CH_2CH_2O)_eR^{23}$, $-(CH_2)_a(CH_2CH_2O)_b(CH_2)_cSO_2NR^{16} (CH_2)_d(CH_2CH_2O)R^{24}$, $-(CH_2)_a(CH_2CH_2O)_b (CH_2)_cNR^{17}CO(CH_2)_d(CH_2CH_2O)_eR^{25}$, $-(CH_2)_a (CH_2CH_2O)_b(CH_2)_cNR^{18}CO_2(CH_2)_d(CH_2CH_2O)_eR^{26}$, $-(CH_2)_a(CH_2CH_2O)_b(CH_2)_cOC(O)NR^{19}(CH_2)_d (CH_2CH_2O)_eR^{27}$, or any combination thereof. Each of $R^8$ to $R^{19}$ can independently be $-H$ or $-CH_3$. Each of $R^{20}$ to $R^{27}$ can independently be $-H$, $-CH_3$, $-(CH_2)_fNR^{28}C(O)NR^{29} (CH_2)_g(CH_2CH_2O)_hR^{38}$, $-(CH_2)_fNR^{30}CSNR^{31}(CH_2)_g (CH_2CH_2O)_hR^{39}$, $-(CH_2)_fC(O)NR^{32}(CH_2)_g(CH_2 CH_2O)_hR^{40}$, $-(CH_2)_fS(O)_2NR^{31}(CH_2)_g(CH_2CH_2O)_hR^{41}$, $-(CH_2)_fNR^{34}S(O)_2(CH_2)_g(CH_2CH_2O)_hR^{42}$, $-(CH_2)_f NR^{35}C(O)(CH_2)_g(CH_2CH_2O)_hR^{43}$, $-(CH_2)_fNR^{36}C(O)O (CH_2)_g(CH_2CH_2O)_hR^{44}$, $-(CH_2)_fOC(O)NR^{37}(CH_2)_g (CH_2CH_2O)_hR^{45}$, $-CO(AA)$, $-CONH(PS)$, or any combination thereof. Each of $R^{28}$ to $R^{31}$ can independently be —H or —$CH_3$. Each of $R^{38}$ to $R^{45}$ can independently be —H, —$CH_3$, —CO(AA) or —CONH(PS).

Still referring to pyrazine derivatives of Formulas I and II above, each of $Y^1$ and $Y^2$ can independently be —$OR^{46}$, —$SR^{47}$, —$NR^{48}R^{49}$, —$N(R^{50})COR^{51}$, —$P(R^{52})_3$, —$P(OR^{53})_3$, or

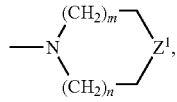

$Z^1$ can be a single bond, —$CR^{54}R^{55}$, —O, —$NR^{56}$, —$NCOR^{57}$, —S, —SO, or —$SO_2$. Each of $R^{46}$ to $R^{57}$ can independently be —H, —$(CH_2)_cOR^{68}$, —$CH_2(CHOH)_cR^{69}$, —$CH_2(CHOH)_cCO_2H$, —$(CHCO_2H)_cCO_2H$, —$(CH_2)_cNR^{70}R^{71}$, —$CH[(CH_2)_fNH_2]_cCO_2H$, —$CH[(CH_2)_fNH_2]_cCH_2OH$, —$CH_2(CHNH_2)_c$ $CH_2NR^{72}R^{73}$, —$(CH_2CH_2O)_eR^{74}$, —$(CH_2)_cCO$ $(CH_2CH_2O)_eR^{75}$, —$(CH_2)_i(CH_2CH_2O)_j(CH_2)_kNR^{58}C(O)$ $NR^{59}(CH_2)_f(CH_2CH_2O)_oR^{76}$, —$(CH_2)_i(CH_2CH_2O)_j$ $(CH_2)_kNR^{60}C(S)NR^{61}(CH_2)_f(CH_2CH_2O)_oR^{77}$, —$(CH_2)_i$ $(CH_2CH_2O)_j(CH_2)_kC(O)NR^{62}(CH_2)_f(CH_2CH_2O)_oR^{78}$, —$(CH_2)_i(CH_2CH_2O)_j(CH_2)_kS(O)_2NR^{63}(CH_2)_f(CH_2CH_2O)$ $OR^{79}$, —$(CH_2)_i(CH_2CH_2O)_j(CH_2)_kNR^{64}S(O)_2(CH_2)_f$ $(CH_2CH_2O)_oR^{80}$, —$(CH_2)_i(CH_2CH_2O)_j(CH_2)_kNR^{65}C(O)$ $(CH_2)_f(CH_2CH_2O)_oR^{81}$, —$(CH_2)_i(CH_2CH_2O)_j$ $(CH_2)_kNR^{66}C(O)O(CH_2)_f(CH_2CH_2O)_oR^{12}$, —$(CH_2)_i$ $(CH_2CH_2O)_j(CH_2)_kOC(O)NR^{67}(CH_2)_f(CH_2CH_2O)OR^{83}$, —$(CH_2)_aSO_3H$, —$(CH_2)_aSO_3^-$, —$(CH_2)_aOSO_3H$, —$(CH_2)_aOSO_3^-$, —$(CH_2)_aNHSO_3H$, —$(CH_2)_aNHSO_3^-$, —$(CH_2)_aPO_3H_2$, —$(CH_2)_aPO_3H^-$, —$(CH_2)_aPO_3^=$, —$(CH_2)_aOPO_3H_2$, —$(CH_2)_aOPO_3H^-$, —$(CH_2)_aOPO_3$, or any combination thereof. Each of $R^{58}$ to $R^{67}$ can independently be —H or —$CH_3$. Each of $R^{68}$ to $R^{83}$ can independently be —H, —$CH_3$, —$(CH_2)_pNR^{81}C(O)NR^{82}(CH_2)_q$ $(CH_2CH_2O)_sR^{77}$, —$(CH_2)_pC(O)NR^{83}(CH_2)_q(CH_2$ $CH_2O)_sR^{79}$, —$(CH_2)_pS(O)_2NR^{84}(CH_2)_q(CH_2CH_2O)_sR^{81}$, —$(CH_2)_pNR^{85}S(O)_2(CH_2)_q(CH_2CH_2O)_sR^{83}$, —$(CH_2)_p$ $NR^{86}C(O)(CH_2)_q(CH_2CH_2O)_sR^{85}$, —$(CH_2)_pNR^{86}C(O)O$ $(CH_2)_q(CH_2CH_2O)_sR^{87}$, —$(CH_2)_pOC(O)NR^{88}(CH_2)_q$ $(CH_2CH_2O)_sR^{89}$, or any combination thereof. Each of $R^{81}$ to $R^{89}$ can independently be —H or —$CH_3$.

(AA) is a polypeptide chain that includes one or more natural or unnatural α-amino acids linked together by peptide bonds. (PS) is a sulfated or non-sulfated polysaccharide chain comprising one or more monosaccharide units connected by glycosidic linkages.

Still referring to pyrazine derivatives of Formulas I and II, each of 'a', 'd', 'g', 'i', 'l', and 'q' can independently be 0, 1, 2, 3, 4, 5, 6, 7, 8, 9 or 10. In addition, each of 'c', 'f', 'k', and 'p' can independently be 1, 2, 3, 4, 5, 6, 7, 8, 9 or 10. Each of 'b' and 'j' can independently be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100. Further, each of 'e', 'h', 'o', and 's' can independently be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In addition, each of 'm' and 'n' can independently be 1, 2 or 3.

With regard to pyrazine derivatives of the fifth embodiment, each of $X^1$ and $X^2$ can independently be —$CO_2R^1$, —$COR^2$, or —$CONR^7R^9$ in some embodiments. In other embodiments, each of $X^1$ and $X^2$ can independently be —$CO_2R^1$ or —$CONR^7R^9$.

$Y^1$ and $Y^2$ may independently be —$NR^{48}R^{49}$ or

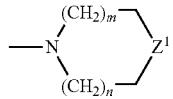

in some embodiments. For instance, in some embodiments, each of $Y^1$ and $Y^2$ can be —$NR^{48}R^{49}$.

In some embodiments, $Z^1$ may be —O, —$NR^{56}$, —S, —SO or —$SO_2$. For instance, in some embodiments, $Z^1$ may be —O or —$NR^{56}$.

In some embodiments, each of $R^1$ to $R^7$ may independently be —$(CH_2)_aNR^{10}CONR^{11}(CH_2)_b(CH_2CH_2O)_cR^{20}$, —$(CH_2)_aCONR^{14}(CH_2)_b(CH_2CH_2O)_cR^{22}$, —$(CH_2)_a$ $SO_2NR^{15}(CH_2)_b(CH_2CH_2O)_eR^{23}$, —$(CH_2)_aSO_2NR^{16}$ $(CH_2)_b(CH_2CH_2O)_cR^{24}$, —$(CH_2)_aNR^{17}CO(CH_2)_b$ $(CH_2CH_2O)R^{25}$, —$(CH_2)_aNR^{18}CO_2(CH_2)_b(CH_2CH_2O)$ $R^{26}$, or —$(CH_2)_aOC(O)NR^{19}(CH_2)_b(CH_2CH_2O)_cR^{27}$. For instance, in some embodiments, each of $R^1$ to $R^6$ may be —$(CH_2)_aNR^{10}CONR^{11}(CH_2)_b(CH_2CH_2O)_cR^{20}$. In other embodiments, each of $R^1$ to $R^7$ may independently be —$(CH_2)_a(CH_2CH_2O)_b(CH_2)_cNR^2CSNR^{31}(CH_2)_d$ $(CH_2CH_2O)_eR^{21}$, —$(CH_2)_a(CH_2CH_2O)_b(CH_2)_cCONR^{14}$ $(CH_2)_d(CH_2CH_2O)_eR^{22}$, —$(CH_2)_a(CH_2CH_2O)_b$ $(CH_2)_cNR^{15}SO_2(CH_2)_d(CH_2CH_2O)_eR^{23}$, —$(CH_2)_a$ $(CH_2CH_2O)_b(CH_2)_cSO_2NR^{16}(CH_2)_d(CH_2CH_2O)_eR^{24}$, —$(CH_2)_a(CH_2CH_2O)_b(CH_2)_eNR^{18}CO_2(CH_2)_d(CH_2$ $CH_2O)_eR^{26}$, or —$(CH_2)_a(CH_2CH_2O)_b(CH_2)_cOC(O)NR^{19}$ $(CH_2)_d(CH_2CH_2O)_eR^{27}$.

In some embodiments, each of $R^{20}$ to $R^{27}$ may independently be —H, —$CH_3$, —$(CH_2)_fNR^{30}CSNR^{31}(CH_2)_g$ $(CH_2CH_2O)_hR^{39}$, —$(CH_2)_fC(O)NR^{32}(CH_2)_g(CH_2$ $CH_2O)_hR^{40}$, —$(CH_2)_fS(O)_2NR^{33}(CH_2)_g(CH_2CH_2O)_hR^{41}$, —$(CH_2)_fNR^{34}S(O)_2(CH_2)_g(CH_2CH_2O)_hR^{42}$, —$(CH_2)_f$ $NR^{36}C(O)O(CH_2)_g(CH_2CH_2O)_hR^{44}$, —$(CH_2)_fOC(O)NR^{37}$ $(CH_2)_g(CH_2CH_2O)_hR^{45}$, —CO(AA), or —CONH(PS).

In some embodiments, each of $R^{38}$ to $R^{45}$ may independently be —H or —$CH_3$.

In some embodiments, $R^{46}$ to $R^{57}$ may independently be —H, —$(CH_2)OR^{68}$, —$CH_2(CHOH)R^{69}$, —$CH_2$ $(CHOH)_cCO_2H$, —$(CHCO_2H)_cCO_2H$, —$(CH_2)_cR^{70}R^{71}$, —$CH[(CH_2)_fNH_2]_cCO_2H$, —$CH[(CH_2)_fNH_2]_cCH_2OH$, —$CH_2(CHNH_2)_cCH_2NR^{72}R^{73}$, —$(CH_2CH_2O)_eR^{74}$, —$(CH_2)_cCO(CH_2CH_2O)_eR^{75}$, —$(CH_2)_i(CH_2CH_2O)_j$ $(CH_2)_kNR^{58}C(O)N^{59}(CH_2)_f(CH_2CH_2O)_oR^{76}$, —$(CH_2)_i$ $(CH_2CH_2O)_j(CH_2)_kNR^{60}C(S)NR^{61}(CH_2)_f(CH_2CH_2O)_oR^{77}$, —$(CH_2)_i(CH_2CH_2O)_j(CH_2)_kC(O)NR^{62}(CH_2)_f(CH_2$ $CH_2O)_oR^{78}$, —$(CH_2)_i(CH_2CH_2O)_j(CH_2)_kS(O)_2NR^{63}(CH_2)_f$ $(CH_2CH_2O)R^{79}$, —$(CH_2)_i(CH_2CH_2O)_j(CH_2)_kNR^{64}S(O)_2$ $(CH_2)_f(CH_2CH_2O)_oR^{79}$, —$(CH_2)_i(CH_2CH_2O)_j$ $(CH_2)_kNR^{65}C(O)(CH_2)_f(CH_2CH_2O)_oR^{81}$, —$(CH_2)_i$ $(CH_2CH_2O)_j(CH_2)_kNR^{66}C(O)O(CH_2)_f(CH_2CH_2O)_oR^{82}$, —$(CH_2)_i(CH_2CH_2O)_j(CH_2)_kOC(O)NR^{67}(CH_2)_f$ $(CH_2CH_2O)_oR^{83}$, —$(CH_2)_aSO_3H$, —$(CH_2)_aSO_3^-$, —$(CH_2)_aOSO_3H$, —$(CH_2)_aOSO_3^-$, —$(CH_2)_aNHSO_3H$, or —$(CH_2)_aNHSO_3^-$.

As stated above, (AA) is polypeptide chain including one or more natural or unnatural α-amino acids linked together by peptide bonds. The polypeptide chain (AA) may be a homopolypeptide chain or a heteropolypeptide chain, and may be any appropriate length. For instance, in some embodiments, the polypeptide chain may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 α-amino acid(s), 1 to 90 α-amino acid(s), 1 to 80 α-amino acid(s), 1 to 70 α-amino acid(s), 1 to 60 α-amino acid(s), 1 to 50 α-amino acid(s), 1 to 40 α-amino acid(s), 1 to 30 α-amino acid(s), 1 to 20 α-amino acid(s), or even 1 to 10 α-amino acid(s). In some embodiments, the α-amino acids of the polypeptide chain (AA) are selected from aspartic acid, asparigine, arginine, histidine, lysine, glutamic acid, glutamine, serine, and homoserine. In some embodiments, the α-amino acids of the polypeptide chain (AA) are selected from aspartic acid, glutamic acid, serine, and homoserine. In some embodiments, the polypeptide chain (AA) refers to a single amino (e.g., either aspartic acid or serine).

As stated above, (PS) is a sulfated or non-sulfated polysaccharide chain including one or more monosaccharide units connected by glycosidic linkages. The polysaccharide chain (PS) may be any appropriate length. For instance, in some embodiments, the polysaccharide chain may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 monosaccharide unit(s), 1 to 90 monosaccharide unit(s), 1 to 80 monosaccharide unit(s), 1 to 70 monosaccharide unit(s), 1 to 60 monosaccharide unit(s), 1 to 50 monosaccharide unit(s), 1 to 40 monosaccharide unit(s), 1 to 30 monosaccharide unit(s), 1 to 20 monosaccharide unit(s), or even 1 to 10 monosaccharide unit(s). In some embodiments, the polysaccharide chain (PS) is a homopolysaccharide chain consisting of either pentose or hexose monosaccharide units. In other embodiments, the polysaccharide chain (PS) is a heteropolysaccharide chain consisting of one or both pentose and hexose monosaccharide units. In some embodiments, the monosaccharide units of the polysaccharide chain (PS) are selected from the group consisting of glucose, fructose, mannose, xylose and ribose. In some embodiments, the polysaccharide chain (PS) refers to a single monosaccharide unit (e.g., either glucose or fructose).

Still referring to pyrazine derivatives of Formulas I and II, in some embodiments, each of 'a', 'd', 'g', 'i', 'l', and 'q' may independently be 1, 2, 3, 4, 5 or 6. Each of 'e', 'h', 'o', and 's' may independently be 1, 2, 3, 4, 5, 6, 7, 8, 9, 10, 11, 12, 13, 14, 15, 16, 17, 13, 19 or 20 in some embodiments. Similarly, in some embodiments, each of 'b' and 'j' may independently be 0, 1, 2, 3, 4, 5, 6, 7, 8, 9, 10, 11, 12, 13, 14, 15, 16, 17, 18, 19 or 20. In some embodiments, each of 'm' and 'n' may independently be 1 or 2.

Any of the pyrazine derivatives described above may exhibit any appropriate molecular weight. For instance, in some embodiments, a pyrazine derivative of the invention may have a molecular weight of no more than about 20000. In other embodiments, a pyrazine derivative of the invention may have a molecular weight of no more than about 15000, 14000, 13000, 12000, 11000, 10000, 9000, 8000, 7000, 6000, 5000, 4500, 4000, 3500, 3000, 2500, 2000, 1500, 1000, 900, 800, 700, 600, 500, 400, 300, 200, or even 100. Other embodiments may have molecular weights that are greater than about 20000.

Yet another aspect of the invention is directed to methods of using pyrazine derivatives described herein. In such methods, a pyrazine derivative is administered to a patient and utilized in a medical photodiagnostic and/or imaging procedure (e.g., assessing renal function).

In accordance with one protocol for assessing physiological function of body cells, an effective amount of a pyrazine derivative described herein is administered into a body of a patient. An appropriate dosage of the pyrazine derivate that is administered to the patient is readily determinable by one of ordinary skill in the art and may vary according to the clinical procedure contemplated (e.g., ranging from about 1 nanomolar to about 100 micromolar). The administration of the pyrazine derivative to the patient may occur in any of a number of appropriate fashions including, but not limited to: (1) intravenous, intraperitoneal, or subcutaneous injection or infusion; (2) oral administration; (3) transdermal absorption through the skin; and (4) inhalation.

Pyrazine derivatives of this invention may be administered as solutions in most pharmaceutically acceptable intravenous vehicles known in the art. Pharmaceutically acceptable vehicles that are well known to those skilled in the art include, but are not limited to, 0.01-0.1 M phosphate buffer or 0.8% saline. Additionally, pharmaceutically acceptable carriers may be aqueous or non-aqueous solutions, suspensions, emulsions, or appropriate combinations thereof. Examples of non-aqueous solvents are propylene glycol, polyethylene glycol, vegetable oils such as olive oil, and injectable organic esters such as ethyl oleate. Examples of aqueous carriers are water, alcoholic/aqueous solutions, emulsions or suspensions, including saline and buffered media. Exemplary parenteral vehicles include sodium chloride solution, Ringer's dextrose, dextrose and sodium chloride, lactated Ringer's or fixed oils. Exemplary intravenous vehicles include fluid and nutrient replenishers, electrolyte replenishers such as those based on Ringer's dextrose, and the like. Preservatives and other additives may be present, such as, for example, antimicrobials, and antioxidants, collating agents, inert gases and the like.

Suitable diluents, preservatives, solubilizers, emulsifiers, adjuvant and/or carriers are also suitable excipients. Such compositions tend to be liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions may likely influence the physical state, solubility, stability, rate of in vivo release, and/or rate of in vivo clearance.

Still referring to the above-mentioned method of use, the pyrazine derivative is exposed to visible and/or near infrared light. This exposure of the pyrazine derivate to light may occur at any appropriate time but preferably occurs while the pyrazine derivative is located in the body. Due to this exposure of the pyrazine derivate to the visible and/or infrared light, the pyrazine derivate emanates spectral energy (e.g., visible and/or near infrared light) that may be detected by appropriate detection equipment. The spectral energy emanated from the pyrazine derivative may tend to be a wavelength range greater than a wavelength range of the light to which the pyrazine derivative was exposed. For example, if a given pyrazine derivative absorbs light of about 700 nm, the pyrazine derivative may emit light of about 745 nm.

Detection of a pyrazine derivate (or more particularly, the light emanating therefrom) may be achieved through optical fluorescence, absorbance, and/or light scattering procedures known in the art. In one embodiment, this detection of emanated spectral energy may be characterized as a collection of the emanated spectral energy and a generation of electrical signal indicative of the collected spectral energy. The mechanism(s) utilized to detect the spectral energy from a given pyrazine derivative that is present in the body may be designed to detect only selected wavelengths (or wavelength ranges) and/or may include one or more appropriate spectral filters. Various catheters, endoscopes, ear clips, hand bands, head bands, surface coils, finger probes and the like may be utilized to expose the pyrazine derivative to light and/or to detect light emanating therefrom.[22] This detection of spectral energy may be accomplished at one or more times intermittently or may be substantially continuous.

Renal function of the patient may be determined based on the detected spectral energy. This may be achieved by using data indicative of the detected spectral energy and generating an intensity/time profile indicative of a clearance of the pyrazine derivative from the body. This profile may be correlated to a physiological or pathological condition. For example, the patient's clearance profiles and/or clearance rates may be compared to known clearance profiles and/or rates to assess the patient's renal function and to diagnose the patient's physiological condition. In the case of analyzing the presence of the pyrazine derivative in bodily fluids, concentration/time curves may be generated and analyzed (preferably in real time) using an appropriate microprocessor to diagnose renal function.

Physiological function may be assessed by: (1) comparing differences in manners in which normal and impaired cells remove a pyrazine derivative of the invention from the bloodstream; (2) measuring a rate or an accumulation of a pyrazine derivative of the invention in the organs or tissues; and/or (3) obtaining tomographic images of organs or tissues having a pyrazine derivative of the invention associated therewith. For example, blood pool clearance may be measured non-invasively from convenient surface capillaries such as those found in an ear lobe or a finger or may be measured invasively using an appropriate instrument such as an endovascular catheter. Accumulation of a pyrazine derivative of the invention within cells of interest may be assessed in a similar fashion.

A modified pulmonary artery catheter may also be utilized to, inter alia, make the desired measurements of spectral energy emanating from a pyrazine derivative of the invention. [23] The ability for a pulmonary catheter to detect spectral energy emanating from a pyrazine derivative of the invention is a distinct improvement over current pulmonary artery catheters that measure only intravascular pressures, cardiac output and other derived measures of blood flow. Traditionally, critically ill patients have been managed using only the above-listed parameters, and their treatment has tended to be dependent upon intermittent blood sampling and testing for assessment of renal function. These traditional parameters provide for discontinuous data and are frequently misleading in many patient populations.

Modification of a standard pulmonary artery catheter only requires making a fiber optic sensor thereof wavelength-specific. Catheters that incorporate fiber optic technology for measuring mixed venous oxygen saturation exist currently. In one characterization, it may be said that the modified pulmonary artery catheter incorporates a wavelength-specific optical sensor into a tip of a standard pulmonary artery catheter. This wavelength-specific optical sensor may be utilized to monitor renal function-specific elimination of a designed optically detectable chemical entity such as the pyrazine derivatives of the present invention. Thus, by a method analogous to a dye dilution curve, real-time renal function may be monitored by the disappearance/clearance of an optically detected compound.

Yet another aspect of the invention is directed to pharmaceutically acceptable compositions, each of which includes one or more pyrazine derivatives disclosed herein. The phrase "pharmaceutically acceptable" herein refers substances that are, within the scope of sound medical judgment, suitable for use in contact with relevant tissues of humans and animals without undue toxicity, irritation, allergic response and the like, and are commensurate with a reasonable benefit/risk ratio. These compositions of the invention may include one or more appropriate excipients such as, but not limited to, suitable diluents, preservatives, solubilizers, emulsifiers, adjuvant and/or carriers. One example of a composition of the invention may include at least one pyrazine derivative of Formula I and/or at least one pyrazine derivative of Formula II.

Yet another aspect of the invention is directed to methods of determining renal function using pyrazine derivatives such as those described above (e.g., with regard to Formulas I and II). In these methods, an effective amount of a pyrazine derivative is administered into the body of a patient (e.g., a mammal such as a human or animal subject). Incidentally, an "effective amount" herein generally refers to an amount of pyrazine derivative that is sufficient to enable renal clearance to be analyzed. The pyrazine derivative in the body of the patient is exposed to at least one of visible and near infrared light. Due to this exposure of the pyrazine derivative to the visible and/or infrared light, the pyrazine derivative emanates spectral energy that may be detected by appropriate detection equipment. This spectral energy emanating from the pyrazine derivative may be detected using an appropriate detection mechanism such as an invasive or non-invasive optical probe. Herein, "emanating" or the like refers to spectral energy that is emitted and/or fluoresced from a pyrazine derivative. Renal function may be determined based the spectral energy that is detected. For example, an initial amount of the amount of pyrazine derivative present in the body of a patient may be determined by a magnitude/intensity of light emanated from the pyrazine derivative that is detected (e.g., in the bloodstream). As the pyrazine derivative is cleared from the body, the magnitude/intensity of detected light generally diminishes. Accordingly, a rate at which this magnitude of detected light diminishes may be correlated to a renal clearance rate of the patient. This detection may be done periodically or in substantially real time (providing a substantially continuous monitoring of renal function). Indeed, methods of the present invention enable renal function/clearance to be determined via detecting one or both a change and a rate of change of the detected magnitude of spectral energy (indicative of an amount of the pyrazine derivative that has not been cleared) from the portion of the pyrazine derivative that remains in the body.

Yet another aspect of the invention is directed to a process for producing pyrazine derivatives. In this process, an aminopyrazine compound and a carbonyl compound are combined in the presence of a reducing agent. For example, in some embodiments, a diaminopyrazine and a carbonyl compound can be combined in the presence of a reducing agent to produce an N,N'-alkylated diaminopyrazine.

In some embodiments, the aminopyrazine compound, the carbonyl compound, and a solvent may be combined in the presence of the reducing agent. The various components that are combined may be at any appropriate temperature during the process (e.g., during the combining). Moreover, the process or a portion thereof (e.g., the actual combining of the various components) may take place in an environment of any appropriate temperature. For instance, the temperature of one or more of the various components and/or the environment may be within a range of −20° to 50° C. (inclusive) during the combining in some embodiments. In other words, the temperature can be −20, −19, −18, −17, −16, −15, −14, −13, −12, −11, −10, −9, −8, −7, −6, −5, −4, −3, −2, −1, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 degrees Celsius. In other embodiments, the temperature of one or more of the various components and/or the environment may be within a range of −5° to 30° C. (inclusive) during the combining In other words, the temperature can be −5, −4, −3, −2, −1, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or degrees Celsius.

The carbonyl compound used in the process may be any appropriate carbonyl compound. For instance, in some embodiments, the carbonyl compound may be of Formula III below.

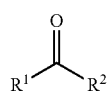

Formula III

In Formula III, each of $R^1$ and $R^2$ is independently hydrogen, $C_1$-$C_{10}$ alkyl, $C_5$-$C_{20}$ aralkyl, $C_1$-$C_{20}$ hydroxyalkyl, $C_2$-$C_{20}$ polyhydroxyalkyl, —$(CH_2)_n$$CO_2R^3$, —$(CH_2CH_2O)_mR^4$, or mono- or poly-saccharide containing 1 to 50 units.

Referring to $R^1$ and $R^2$ of Formula III, m and n may be any appropriate integers. For instance, in some embodiments, each of m and n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In some embodiments, each of m and n may independently be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30. In other embodiments, m and n may independently be 1, 2, 3, 4, 5, 6, 7, 8, 9, 10, 11, 12, 13, 14, 15, 16, 17, 18, 19 or 20. In yet other embodiments, m and n may independently be 1, 2, 3, 4, 5, 6, 7, 8, 9 or 10.

Still referring to $R^1$ and $R^2$ of Formula III, each occurrence of $R^3$ and $R^4$ is independently hydrogen, $C_1$-$C_{10}$ alkyl, $C_5$-$C_{20}$ aralkyl, $C_1$-$C_{10}$ acyl, $C_1$-$C_{20}$ hydroxyalkyl, $C_2$-$C_{20}$ polyhydroxyalkyl, or mono- or poly-saccharide containing 1 to 50 units. For instance, in some embodiments, each of $R^3$ and $R^4$ is independently hydrogen, $C_1$-$C_{10}$ alkyl $C_1$-$C_{20}$ hydroxyalkyl, or $C_2$-$C_{20}$ polyhydroxyalkyl.

The aminopyrazine compound utilized in the process may be any appropriate aminopyrazine compound. For instance, the aminopyrazine compound utilized may be a compound of the following Formula IV or V below.

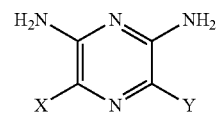

Formula IV

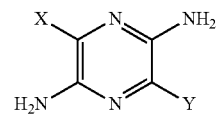

Formula V

With regard to Formulas IV and V above, each X and Y is independently hydrogen, $C_1$-$C_{10}$ alkyl, —$OR^5$, —$SR^6$, —$NR^7R^8$, —$N(R^9)COR^{10}$, halo, trihaloakyl, —CN, —$NO_2$, —CO—Z—$R^{11}$, —$SOR^2$, —$SO_2R^{13}$, —$SO_2OR^{14}$, or —$PO_3R^{15}R^{16}$. Z is a single bond, —O—, —$NR^{17}$—, —NH$(CH_2)_p$NH—, —NH$(CH_2)_p$O—, —NH$(CH_2)_p$CO—, —NH$(CH_2)_p$NHCO—, —NH$(CH_2)_p$CONH—, —NH$(CH_2)_p$NHCONH—, —NH$(CH_2)_p$NHCSNH—, or —NH$(CH_2)_p$NHCO_2—. Each of $R^5$ to $R^{17}$ is independently hydrogen, $C_1$-$C_{10}$ alkyl, $C_5$-$C_{20}$ aralkyl, $C_1$-$C_{10}$ acyl, $C_1$-$C_{20}$ hydroxyalkyl, $C_2$-$C_{20}$ polyhydroxyalkyl, —$CH_2CH_2O)_qR^{18}$, or mono- or poly-saccharide containing 1 to 50 units. $R^{18}$ is hydrogen, $C_1$-$C_{10}$ alkyl, $C_5$-$C_{20}$ aralkyl, $C_1$-$C_{10}$ acyl, $C_1$-$C_{20}$ hydroxyalkyl, $C_2$-$C_{20}$ polyhydroxyalkyl, or mono- or polysaccharide containing 1 to 50 units. The integer p 0, 1, 2, 3, 4, 5 or 6. Further, the integer q is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50.

In some compounds of Formulas IV and V above, each of X and Y may be CN in some embodiments and —CO—Z—$R^{11}$ in other embodiments. In embodiments of compounds of Formulas IV and V that include $R^{11}$, $R^{11}$ of some embodiments may be hydrogen, $C_1$-$C_{10}$ alkyl, $C_1$-$C_{20}$ hydroxyalkyl, or $C_2$-$C_{20}$ polyhydroxyalkyl. When each of X and Y is —CO—Z—$R^{11}$, Z may be —$NR^{17}$— in some embodiments, —NH$(CH_2)_p$NH— in other embodiments, and —NH$(CH_2)_p$CO— in other embodiments. In the case that Z is —$NR^{17}$—, $R^{17}$ of some embodiments may be hydrogen or $C_1$-$C_{10}$ alkyl. In the case that Z is either NH$(CH_2)_p$NH— or —NH$(CH_2)_p$CO—, the integer p of some embodiments may be 0, 1, 2, 3 or 4.

The reducing agent utilized in the process may be any appropriate reducing agent. For instance, in some embodiments, the reducing agent is ammonium formate, diimide, Zn/HCl, sodium triacetoxyborohydride, sodium borohydride, pyridine/borane, lithium aluminium hydride, lithium borohydride, sodium cyanoborohydride, sodium amalgam, $H_2$/Pd/C, $H_2$/Pt/C, $H_2$/Rh/C, $H_2$/Raney® Nickel, or any combination thereof. In some embodiments, the reducing agent includes or is sodium triacetoxyborohydride. In some embodiments, the reducing agent includes or is sodium cyanoborohydride.

In the case that a solvent is utilized in the process, the solvent may be any appropriate solvent such as, for example, water, $C_1$-$C_8$ alcohol, $C_1$-$C_8$ ether, $C_1$-$C_8$ ester, dimethyl formamide, dimethyl acetamide, acetic acid, trifluoroacetic acid, dimethyl sulfoxide, or any combination thereof. In some embodiments, the solvent may be methanol, ethanol, isopropyl alcohol, tetrahydrofuran, dioxane, glyme, dimethyl formamide, dimethyl sulfoxide, or any combination thereof.

The order of addition of reagents in the process may vary (e.g., depending on the nature of the starting materials used). For example, the present process contemplates the addition of the reducing agent to the mixture of the aminopyrazine and the carbonyl compound, and likewise it contemplates the addition of the carbonyl compound to a mixture of the aminopyrazine and the reducing agent, as well as the addition of the aminopyrazine to a mixture of the carbonyl compound and the reducing agent provided that the reducing agent does not substantially decompose the carbonyl compound. In short, any suitable order of addition may be utilized.

Compound 18 below is an N,N'-alkylated diaminopyrazine that was produced using a process described herein and that could be used to assess renal function.

Example 1

Protocol for Assessing Renal Function

An example of an in vivo renal monitoring assembly 10 is shown in FIG. 1 and includes a light source 12 and a data processing system 14. The light source 12 generally includes

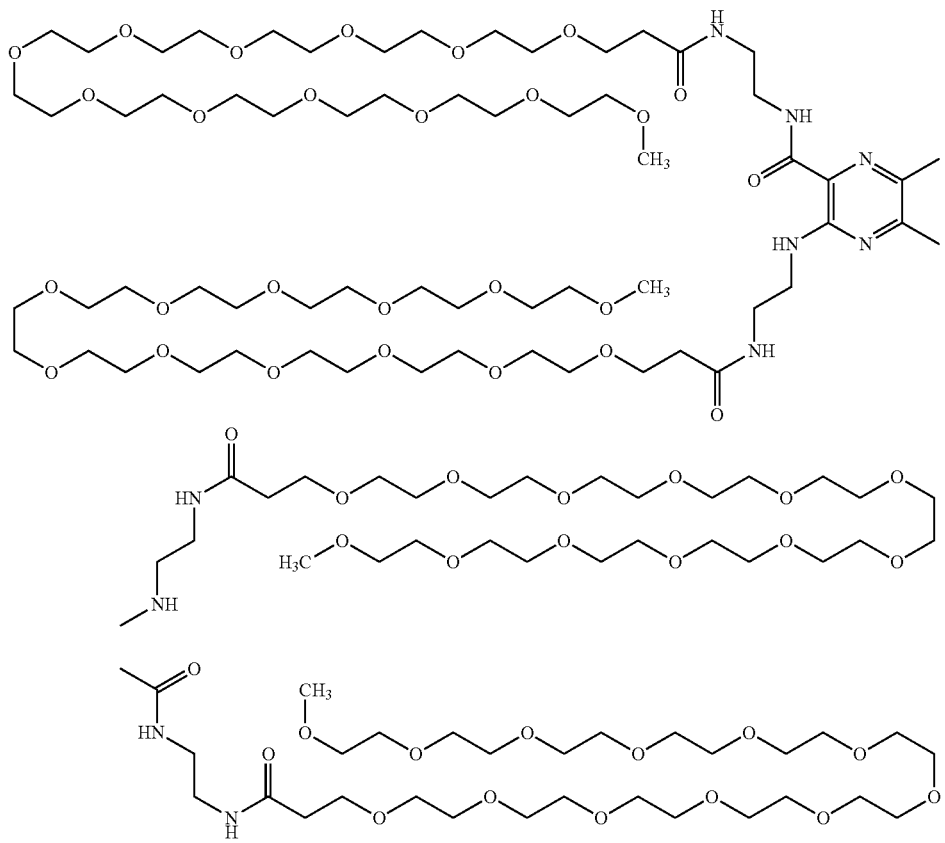

18

Pyrazine derivatives made using a process described herein may be utilized in a number of appropriate methods and procedures (e.g., medical procedures). For instance, pyrazine derivatives made using a process described herein may be utilized in assessing renal function of a medical patient and/or as intermediates in processes for manufacturing pyrazine derivatives and/or compositions that include pyrazine derivatives (e.g., for use in assessing renal function of medical patients).

EXAMPLES

Unless otherwise noted, all reagents were used as supplied. Organic extracts were dried over anhydrous $Na_2SO_4$ and filtered using a fluted filter paper (P8). Solvents were removed on a rotary evaporator under reduced pressure. RP-LC/MS (ESI, positive ion mode) analyses were carried out on a Waters Micromass ZQ system equipped with a PDA detector using either a BDS Hypersil C18 3 μm (50 mm×4.6 mm) or a ThermoElectron Hypersil Gold C18 3 μm (4.6 mm×50 mm) column. Compounds were injected using a gradient condition (5 to 50-95% B/6 min) with a flow rate of 1 ml/min (mobile phase A: 0.05% TFA in $H_2O$; mobile phase B: 0.05% TFA in $CH_3CN$). Chemical shifts are expressed in parts per million (δ) relative to TMS (δ=0) as an internal standard and coupling constants (J) are reported in Hz.

or is interconnected with an appropriate device for exposing at least a portion of a patient's body to light therefrom. Examples of appropriate devices that may be interconnected with or be a part of the light source 12 include, but are not limited to, catheters, endoscopes, fiber optics, ear clips, hand bands, head bands, forehead sensors, surface coils, and finger probes. Indeed, any of a number of devices capable of emitting visible and/or near infrared light of the light source may be employed in the renal monitoring assembly 10.

Still referring to FIG. 1, the data processing system 14 of the renal monitoring assembly 10 may be any appropriate system capable of detecting spectral energy and processing data indicative of the spectral energy. For instance, the data processing system 14 may include one or more lenses (e.g., to direct and/or focus spectral energy), one or more filters (e.g., to filter out undesired wavelengths of spectral energy), a photodiode (e.g., to collect the spectral energy and convert the same into electrical signal indicative of the detected spectral energy), an amplifier (e.g., to amplify electrical signal from the photodiode), and a processing unit (e.g., to process the electrical signal from the photodiode). This data processing system 14 is configured to manipulate collected spectral data and generate an intensity/time profile and/or a concentration/time curve indicative of renal clearance of a pyrazine derivative of the present invention from the patient 20. Indeed, the data processing system 14 may be configured to generate appropriate renal function data by comparing differences in manners in which normal and impaired cells remove the pyrazine derivative from the bloodstream, to determine a rate or an accumulation of the pyrazine derivative in organs or tissues of the patient 20, and/or to provide tomographic images of organs or tissues having the pyrazine derivative associated therewith.

Figure 2:
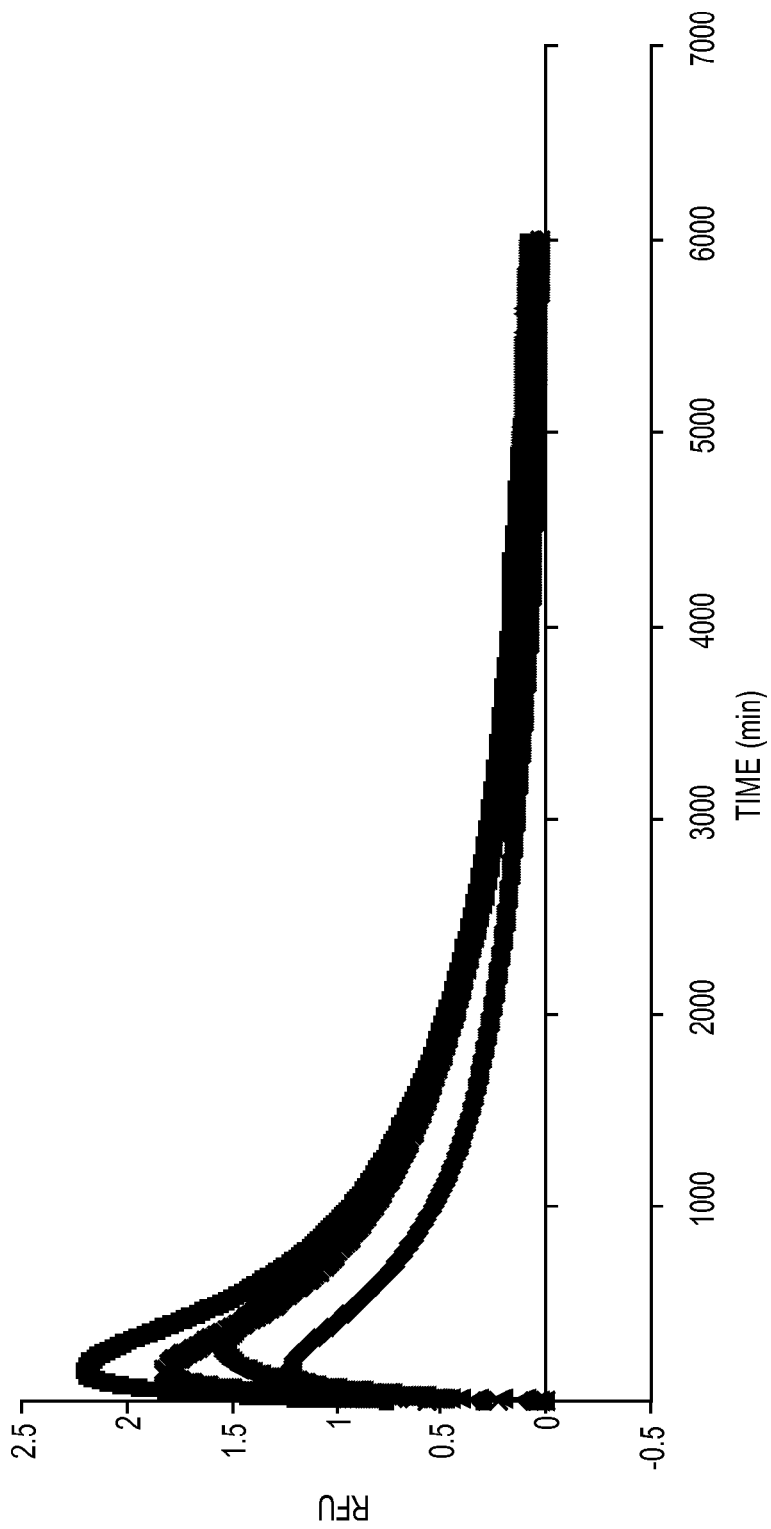
FIG. 2. Illustration of a clearance curve of compound 18 (Formula VI).

FIG. 2 provides a clearance curve in Sprague-Dawley rats for compound 18 of the present invention, the compound being described in greater detail below. Four Sprague-Dawley rats were used to obtain the experimental results depicted in FIG. 2, with each of the four lines of the graph representing data obtained from an individual rat. The rats were injected intravenously with 1 ml of a 2 mmol solution of compound 18 in phosphate-buffered saline CBS), giving a final concentration of compound 18 in each animal of approximately 6 µmol/kg. The presence of compound 18 in each of the animals was monitored over time and measured in Relative Fluorescence Units (RFUs). The clearance curve in FIG. 2 provides RFUs over time for each of the four rats. As shown in FIG. 2, clearance of compound 18 began rapidly in each of the animals, and proceeded at a rapid pace from about 250 minutes to about 750 minutes. The clearance rate then began to level, with complete clearance of compound 18 occurring at approximately 6000 minutes.

Figure 3:
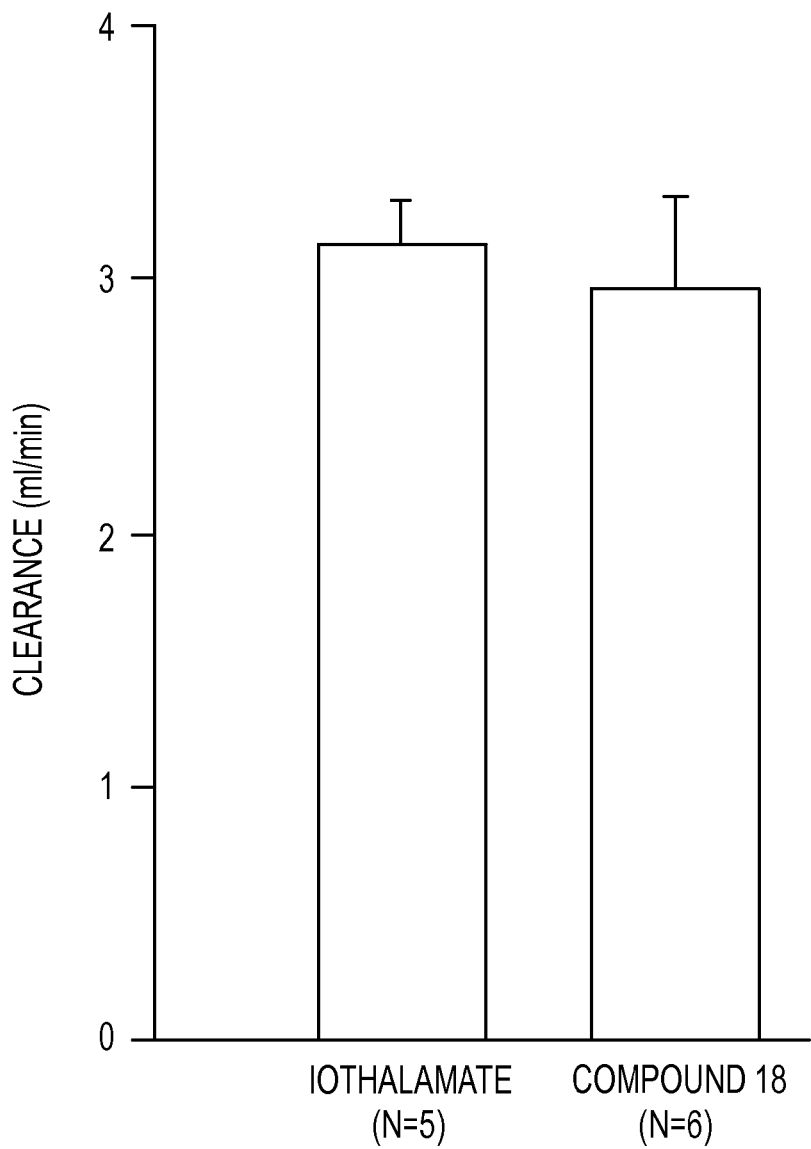
FIG. 3. Comparison of compound 18 and an isothalanate standard.

FIG. 3 provides a bar graph comparison of the clearance rates of an iothalamate reference standard and compound 18. Spraque-Dawley rats were again used as animal models for studying the clearance rates. Iothalamate clearance rates were measured in five rats, whereas clearance rates for compound 18 were measured in six rats. The clearance rates are expressed in FIG. 3 in terms of milliliters per minute. As can be seen from the figure, the clearance rate of iothalamate and compound 18 were observed to be virtually the same. Thus, compound 18 provides clearance rates comparable to the accepted standard of iothalamate, but without the necessity for radiologic or other harmful imaging methods that are commonly used with iothalamate.

In one protocol for determining renal function, an effective amount of a pyrazine derivative of the invention is administered to the patient (e.g., in the form for a pharmaceutically acceptable composition). At least a portion of the body of the patient 20 is exposed to visible and/or near infrared light from the light source 12 as indicated by arrow 16. For instance, the light from the light source 12 may be delivered via a fiber optic that is affixed to an ear of the patient 20. The patient may be exposed to the light from the light source 12 before or after administration of the pyrazine derivative to the patient 20. In some cases, it may be beneficial to generate a background or baseline reading of light being emitted from the body of the patient 20 (due to exposure to the light from the light source 12) before administering the pyrazine derivative to the patient 20. When the pyrazine derivative that is in the body of the patient 20 is exposed to the light from the light source 12, the pyrazine derivative emanates light (indicated by arrow 18) that is detected/collected by the data processing system 14. Initially, administration of the pyrazine derivative to the patient 20 generally enables an initial spectral signal indicative of the initial content of the pyrazine derivative in the patient 20. The spectral signal then tends to decay as a function of time as the pyrazine derivative is cleared from the patient 20. This decay in the spectral signal as a function of time is indicative of the patient's renal function. For example, in a first patient exhibiting healthy/normal renal function, the spectral signal may decay back to a baseline in a time of T.

However, a spectral signal indicative of a second patient exhibiting deficient renal function may decay back to a baseline in a time of T+4 hours. As such, the patient 20 may be exposed to the light from the light source 12 for any amount of time appropriate for providing the desired renal function data. Likewise, the data processing system 14 may be allowed to collect/detect spectral energy for any amount of time appropriate for providing the desired renal function data.

Example 2

Synthesis of Representative Pyrazine PEG Analogues

Unless otherwise noted, all reagents in this Example were used as supplied. Organic extracts were dried over anhydrous $Na_2SO_4$ and filtered using a fluted filter paper (P8). Solvents were removed on a rotary evaporator under reduced pressure. RP-LC/MS (ESI, positive ion mode) analyses were carried out on a Waters Micromass ZQ system equipped with a PDA detector using either a BDS Hypersil C18 3 µm (50 mm×4.6 mm) or a ThermoElectron Hypersil Gold C18 3 µm (4.6 mm×50 mm) column. Compounds were injected using a gradient condition (5 to 50-95% B/6 min) with a flow rate of 1 mL/min (mobile phase A: 0.05% TFA in $H_2O$; mobile phase B: 0.05% TFA in $CH_3CN$). Chemical shifts are expressed in parts per million ($\delta$) relative to TMS ($\delta$=0) as an internal standard and coupling constants (J) are reported in Hz.

A. Diethyl 3,6-bis(benzylamino)pyrazine-2,5-dicarboxylate (7)

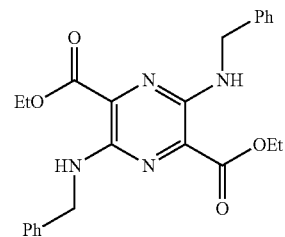

7

To a well-stirred red suspension of diethyl 3,6-diaminopyrazine-2,5-dicarboxylate (0.127 g, 0.500 mmol)[2] in anhyd 1,2-dichloroethane (DCE, 20 mL), benzaldehyde (0.202 mL, 2.00 mmol) was added, and the reaction flask was immersed in an ice bath. Then HOAc (0.115 mL, 2.00 mmol) was added followed by the addition of sodium triacetoxyborohydride (0.424 g, 2.00 mmol) in small portions over a 15 min period. The resulting suspension was slowly allowed to warm to r.t. and stirred overnight (ca. 16 h; RP-LC/MS analysis indicated the presence of some substrate) in an atmosphere of argon. At this stage, the reaction mixture was treated with more benzaldehyde (0.202 mL, 2.00 mmol), HOAc (0.115 mL, 2.00 mmol), and sodium triacetoxyborohydride (0.424 g, 2.00 mmol) as described above, and the reaction was continued overnight (ca. 24 h; RP-LC/MS analysis indicated a complete reaction). The reaction was quenched by a slow addition of satd $NaHCO_3$ (20 mL) while stirring at 0° C. The biphasic mixture was stirred for 30 min and extracted with $CHCl_3$ (3×25 mL). The combined organic extracts were successively washed with satd $NaHCO_3$, $H_2O$, and brine (30 mL each). Removal of the solvent gave 0.200 g of a red solid, which upon flash chromatography over silica gel ($CHCl_3$) afforded Example 1 (0.174 g, 80%) as a dark red powder: $R_f$ 0.49; $^1$H NMR (DMSO-$d_6$) 7.60 (t, 2, J=5.9), 7.42 (dd, 4, J=7.7, 1.7), 7.28-7.18 (m, 6), 4.51 (d, 4, 5.9), 4.32 (q, 4, J=7.1), 1.30 (t, 6, J=7.1); $^{13}$C NMR (DMSO-$d_6$) 165.36, 146.28, 140.07, 128.08, 128.03, 126.65, 124.80, 61.35, 44.39, 44.29, 14.13; RP-LC/MS (ESI) m/z 435.3 (M+H)$^+$, 457.2 (M+Na)$^+$ ($t_R$=5.53 min, 5-95% B). Anal. Calcd for $C_{24}H_{26}N_4O_4$: C, 66.34; H, 6.03; N, 12.89. Found: C, 66.10; H, 5.98; N, 12.67.

B. 3,6-Bis(propylamino)-$N^2$,$N^5$-bis[2-(tert-butoxycarbonyl)aminoethyl]pyrazine-2,5-dicarboxamide (8)

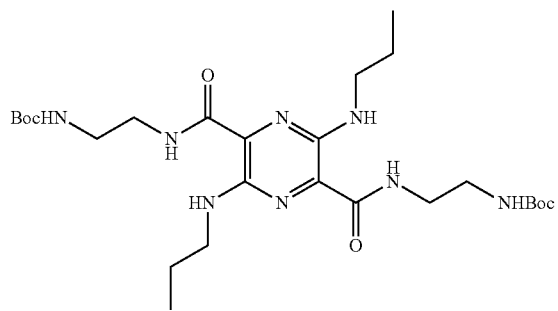

To a partially-dissolved yellow suspension of 3,6-Diamino-$N^2$,$N^5$-bis[2-(tert-butoxycarbonyl)aminoethyl]pyrazine-2,5-dicarboxamide (0.483 g, 1.00 mmol)$^8$ in anhydrous DCE (20 µL), propionaldehyde (0.290 mL, 4.02 mmol) and HOAc (0.290 mL, 5.03 mmol) were added with stirring at 0° C. under argon atmosphere. The resulting somewhat lighter suspension was allowed to stir for 5 min before the addition of sodium triacetoxyborohydride (0.848 g, 4.00 mmol) in small portions over a 10 min period. The reddish suspension was slowly allowed to warm to r.t. and stirred overnight (ca. 19 h) in an atmosphere of argon. The reaction was quenched by a slow addition of satd NaHCO$_3$ (20 mL) at 0° C. The biphasic mixture was stirred for 30 min and extracted with CHCl$_3$ (3×25 mL). The combined organic extracts were successively washed with H$_2$O and brine (50 mL each). Removal of the solvent gave 0.680 g of a red solid, which upon flash chromatography over silica gel [CH$_2$Cl$_2$-EtOAc (17:3 to 3:1, v/v)] afforded Example 2 (0.454 g, 80%) as a crimson red solid: R$_f$ 0.44 [CH$_2$Cl$_2$-EtOAc (7:3, v/v)]; $^1$H NMR (CDCl$_3$) 8.13 (br s, 2), 7.78 (t, 2, J=5.4), 4.87 (br s, 2), 3.53 (q, 4, J=5.9), 3.39-3.34 (quintet, 8), 1.70-1.63 (sextet, 4), 1.42 (s, 18), 1.01 (t, 6, J=7.4); $^{13}$C NMR (CDCl$_3$) 166.84, 156.30, 146.01, 126.07, 79.55, 42.89, 40.44, 39.79, 28.32, 22.75, 11.82; RP-LC/MS (ESI) m/z 567.4 (M+H)$^+$, 589.4 (M+Na)$^+$ ($t_R$=5.17 min, 5-95% B). Anal. Calcd for $C_{26}H_{46}N_8O_6$: C, 55.11; H, 8.18; N, 19.77. Found: C, 55.17; H, 8.31; N, 19.53.

(9) C. 3,6-Bis(benzylamino)-$N^2$,$N^5$-bis[2-(tert-butoxycarbonyl)aminoethyl]pyrazine-2,5-dicarboxamide (9)

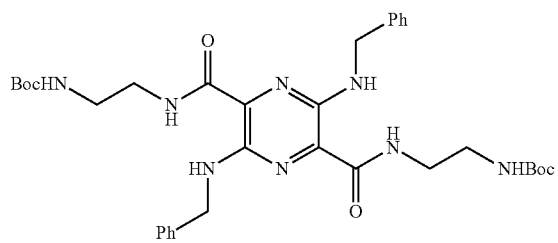

The reaction of 3,6-Diamino-$N^2$,$N^5$-bis[2-(tert-butoxycarbonyl)aminoethyl]pyrazine-2,5-dicarboxamide (0.121 g, 0.250 mmol)$^8$ with benzaldehyde (0.101 mL, 1.00 mmol) in the presence of HOAc (0.058 mL, 1.00 mmol) and sodium triacetoxyborohydride (0.212 g, 1.00 mmol) in DCE (10 mL) was carried out overnight (ca. 16 h) as described in the preparation of Example 2. After the usual work up, the brickred crude product (0.240 g) was subjected to flash chromatography over silica gel [CHCl$_3$-EtOAc (4:1, v/v)], and the residue triturated with anhyd Et$_2$O to give Example 3 (0.119 g, 72%) as an orange powder: R$_f$ 0.40 [CHCl$_3$-EtOAc (7:3, v/v)]; $^1$H NMR (CDCl$_3$) 8.20 (br t, 2, J=5.0), 7.76 (br t, 2), 7.37-7.30 (m, 8), 7.25-7.21 (m, 2), 4.77 (br s, 2), 4.58 (d, 4, J=5.4), 3.44-3.40 (br q, 4), 3.31-3.25 (br q, 4), 1.43 (s, 18); RP-LC/MS (ESI) m/z 663.2 (M+H)$^+$, 685.2 (M+Na)$^+$ ($t_R$=4.30 min, 50-95% B). Anal. Calcd for $C_{34}H_{46}N_8O_6$: C, 61.61; H, 7.00; N, 16.91. Found: C, 61.72; H, 7.07; N, 16.89.

D. 3,6-Bis(4-methoxybenzylamino)-$N^2$,$N^5$-bis[2-(tert-butoxycarbonyl)aminoethyl]pyrazine-2,5-dicarboxamide (10)

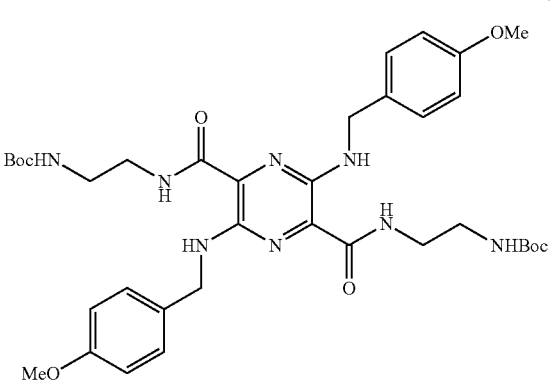

The reaction of 3,6-Diamino-$N^2$,$N^5$-bis[2-(tert-butoxycarbonyl)aminoethyl]pyrazine-2,5-dicarboxamide (0.483 g, 1.00 mmol)$^8$ with 4-methoxybenzaldehyde (0.485 mL, 4.00 mmol) in the presence of HOAc (0.230 mL, 4.00 mmol) and sodium triacetoxyborohydride (0.848 g, 4.00 mmol) in DCE (25 mL) was carried out overnight as described in the preparation of Example 2. After the usual work up, the brick-red crude product (1.14 g) was subjected to flash chromatography over silica gel [CHCl$_3$-EtOAc (3:1, v/v)], and the material obtained was recrystallized from EtOAc-Et$_2$O to give Example 4 (0.615 g, 85%) as an orange-red microcrystalline solid: R$_f$ 0.30 [CHCl$_3$-EtOAc (7:3, v/v)]; $^1$H NMR (CDCl$_3$) 8.14 (br t, 2, J=5.0), 7.90 (br t, 2), 7.28 (d, 4, J=8.5), 6.86 (d, 4, J=8.5), 4.82 (br t, 2), 4.52 (d, 4, J=5.4), 3.78 (s, 6), 3.46-3.43 (br q, 4), 3.33-3.28 (br q, 4), 1.42 (s, 18); RP-LC/MS (ESI) m/z 723.3 (M+H), 745.3 (M+Na)$^+$ ($t_R$=4.08 min, 50-95% B). Anal. Calcd for $C_{36}H_{50}N_8O_8$: C, 59.82; H, 6.97; N, 15.50. Found: C, 60.01; H, 7.05; N, 15.43.

E. 3,6-Bis(4-nitrobenzylamino)-$N^2$,$N^5$-bis[2-(tert-butoxycarbonyl)aminoethyl]pyrazine-2,5-dicarboxamide (11)

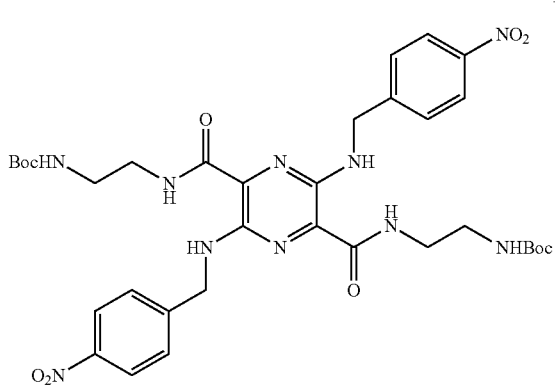

The reaction of 3,6-Diamino-$N^2$,$N^5$-bis[2-(tert-butoxycarbonyl)aminoethyl]pyrazine-2,5-dicarboxamide (0.121 g, 0.250 mmol)[8] with 4-nitrobenzaldehyde (0.151 mL, 1.00 mmol) in the presence of HOAc (0.058 mL, 1.00 mmol) and sodium triacetoxyborohydride (0.212 g, 1.00 mmol) in DCE (10 mL) was carried out overnight (ca. 18 h) as described in the preparation of Example 2. After the usual work up, the brick-red crude product (0.260 g) was subjected to flash chromatography over silica gel [CHCl$_3$-EtOAc (7:3, v/v)], and the residue recrystallized from EtOAc-Et$_2$O to give Example 5 (0.155 g, 82%) as an orange microcrystalline solid: $R_f$ 0.33 [CHCl$_3$-EtOAc (1:1, v/v)]; $^1$H NMR (CDCl$_3$) 8.44 (br t, 2), 8.18 (d, 4, J=8.7), 8.03 (br s, 2), 7.57 (d, 4, J=8.5), 4.78 (br m, 6), 3.46-3.42 (br q, 4), 3.36-3.30 (br m, 4), 1.39 (s, 18); RP-LC/MS (ESI) m/z 753.2 (M+H)$^+$, 775.1 (M+Na)$^+$ ($t_R$=4.02 min, 50-95% B). Anal. Calcd for C$_{34}$H$_{44}$N$_{10}$O$_{10}$: C, 54.25; H, 5.89; N, 18.61. Found: C, 54.20; H, 5.97; N, 18.32.

F. 3,6-Bis(cyclohexylamino)-$N^2$,$N^5$-bis[2-(tert-butoxycarbonyl)aminoethyl]pyrazine-2,5-dicarboxamide (12)

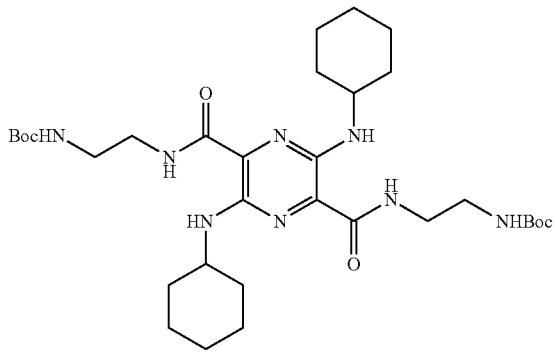

To a partially-dissolved yellow suspension of 3,6-Diamino-$N^2$,$N^5$-bis[2-(tert-butoxycarbonyl)aminoethyl]pyrazine-2,5-dicarboxamide (0.121 g, 0.250 mmol)$_g$ in anhyd DCE (10 mL), cyclohexanone (0.104 mL, 1.00 mmol) was added, and the reaction flask was immersed in an ice bath. Then HOAc (0.058 mL, 1.00 mmol) was added followed by the addition of sodium triacetoxyborohydride (0.212 g, 1.00 mmol) in small portions over a 10 min period. The resulting suspension was slowly allowed to warm to r.t. and stirred overnight (ca. 17 h; RP-LC/MS analysis indicated intact substrate) in an atmosphere of N$_2$. At this stage, the reaction mixture was treated with more cyclohexanone (0.104 mL, 1.00 mmol), HOAc (0.058 mL, 1.00 mmol), and sodium triacetoxyborohydride (0.212 g, 1.00 mmol) as described above, and the reaction was continued for 48 h (RP-LC/MS analysis indicated small amounts of substrate). Similar quantities of the reagents were added once again and the reaction was continued over the weekend (RP-LC/MS analysis indicated a complete reaction). After the usual work up described in Example 2, the crude product (0.456 g) obtained was subjected to flash chromatography over silica gel [CHCl$_3$ to CHCl$_3$-EtOAc (17:3, v/v)] to afford Example 6 (0.075 g, 46%) as a crimson red powder: $R_f$ 0.58 [CHCl$_3$-EtOAc (7:3, v/v)]; $^1$H NMR (CDCl$_3$) 8.02 (br t, 2), 7.75 (d, 2, J=7.7), 4.83 (br t, 2), 3.90-3.76 (br m, 2), 3.52 (q, 4, J=5.9), 3.34 (q, 4, J=5.9), 2.02-1.20 (m, 38, includes Boc singlet at δ 1.42); $^{13}$C NMR (CDCl$_3$) 166.51, 156.35, 144.79, 125.75, 79.42, 48.90, 40.36, 39.52, 32.82, 28.27, 25.92, 24.58; RP-LC/MS (ESI) m/z 647.5 (M+H)$^+$ ($t_R$=5.36 min, 30-95% B). HRMS (ESI) m/z calcd for C$_{32}$H$_{55}$N$_8$O$_6$ (M+1)$^+$ 647.4239, found 647.4238.

The byproducts of the reaction, 0.040 g (27%) of 3-(cyclohexylamino)-6-(ethylamino)-$N^2$,$N^5$-bis[2H-(tert-butoxycarbonyl)aminoethyl]pyrazine-2,5-dicarboxamide [$^1$H NMR (CDCl$_3$) 8.16 (br t, 1), 8.01 (br t, 1), 7.79 (d, 1, J=7.7), 7.63 (t, 1, J=5.1), 4.83 (br s, 2), 3.83 (br m, 1), 3.55-3.34 (m, 10), 1.99-1.21 (m, 31, include Boc singlet at δ 1.42 and Me triplet at (1.27); RP-LC/MS (ESI) m/z 593.4 (M+H)$^+$ ($t_R$=4.88 min, 30-95% B)] and 0.010 g (7%) of 3,6-bis(ethylamino)-$N^2$,$N^5$-bis[2-(tert-butoxycarbonyl)aminoethyl]pyrazine-2,5-dicarboxamide [$^1$H NMR (CDCl$_3$) 8.17 (br t, 2), 7.67 (t, 2, J=5.0), 4.86 (br t, 2), 3.55-3.33 (m, 12), 1.42 (s, 18), 1.27 (t, 6, J=7.2); RP-LC/MS (ESI) m/z 539.3 (M+H)$^+$, 561.5 (M+Na)$^+$ ($t_R$=4.34 min, 30-95% B)], were also isolated in the above chromatography.

G. Dimethyl 4,4'-[3,6-bis{2-(tert-butoxycarbonylamino)ethylcarbamoyl}pyrazine-2,5-diyl]bis(azanediyl)dibutanoate (13)

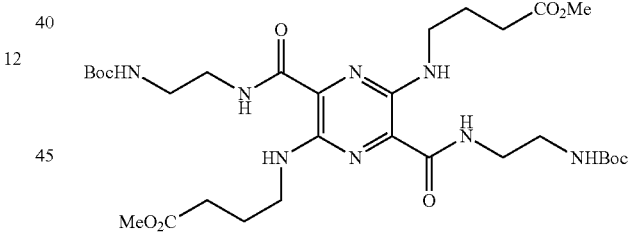

The reaction of 3,6-Diamino-$N^2$,$N^5$-bis[2-(tert-butoxycarbonyl)aminoethyl]pyrazine-2,5-dicarboxamide (0.965 g, 2.00 mmol)[8] with methyl 4-oxobutanoate (0.838 mL, 8.00 mmol) in the presence of HOAc (0.460 mL, 7.98 mmol) and sodium triacetoxyborohydride (1.70 g, 8.00 mmol) in DCE (40 mL) was carried out overnight (ca. 20 h) as described in the preparation of Example 2. After the usual work up, the orange crude product (1.74 g) was subjected to flash chromatography over silica gel [CHCl$_3$-EtOAc (7:3, v/v)] to give Example 7 (1.30 g, 95%) as an orange-red powder: $R_f$ 0.33 [CHCl$_3$-EtOAc (1:1, v/v)]; $^1$H NMR (CDCl$_3$) 8.66 (t, 2, J=5.9), 7.93 (t, 2, J=6.0), 5.21 (br t, 2), 3.67 (s, 6), 3.56 (q, 4, J=5.8), 3.46-3.30 (m, 8), 2.42 (t, 4, J=6.5), 1.99-1.89 (quintet, 4), 1.41 (s, 18); $^{13}$C NMR (CDCl$_3$) 174.40, 166.70, 156.00, 145.63, 126.09, 79.17, 51.82, 40.81, 40.39, 39.53, 30.89, 28.43, 24.44; RP-LC/MS (ESI) m/z 683.3 (M+H)$^+$, 705.3 (M+Na)$^+$ ($t_R$=4.75 min, 15-95% B). HRMS (ESI) m/z calcd for C$_{30}$H$_{51}$N$_8$O$_{10}$ (M+H)$^+$ 683.3723, found 683.3719.

H. 3,6-Bis[2-(tert-butoxycarbonylamino)ethylamino]-$N^2,N^5$-bis[2-(tert-butoxycarbonyl)aminoethyl]pyrazine-2,5-dicarboxamide (14)

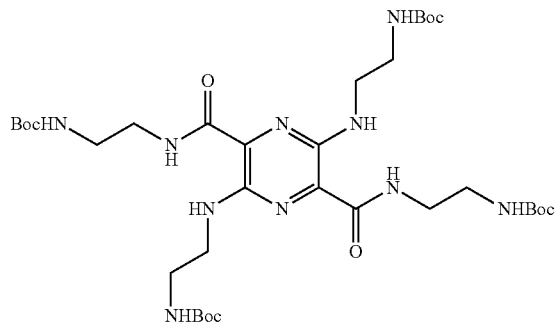

14

To a partially-dissolved yellow suspension of 3,6-Diamino-$N^2,N^5$-bis[2-(tert-butoxycarbonyl)aminoethyl]pyrazine-2,5-dicarboxamide (0.483 g, 1.00 mmol)[8] in anhyd DCE (20 mL), N-Boc-2-aminoacetaldehyde (0.382 g, 2.40 mmol) was added, and the reaction flask was immersed in an ice bath. Then HOAc (0.120 mL, 2.08 mmol) was added followed by the addition of sodium triacetoxyborohydride (0.636 g, 3.00 mmol) in small portions over a 15 min period. The resulting reddish suspension was slowly allowed to warm to r.t. and stirred overnight (ca. 16 h; RP-LCMS analysis indicated some substrate) in an atmosphere of argon. At this stage, the reaction mixture was treated with more N-Boc-2-aminoacetaldehyde (0.191 g, 1.20 mmol), HOAc (0.120 mL, 2.08 mmol), and sodium triacetoxyborohydride (0.212 g, 1.00 mmol) as described above, and the reaction was continued overnight (ca. 25 h; RP-LC/MS analysis indicated a complete reaction). After the usual work up described in Example 2, the crude product (1.04 g) obtained was subjected to flash chromatography over silica gel [CHCl$_3$-EtOAc (1:1, v/v)] to furnish Example 8 (0.813 g, quantitative) as brick-red solid: $R_f$ 0.27; $^1$H NMR (DMSO-d$_6$) 8.81 (t, 2, J=5.9), 7.95 (t, 2, J=5.9), 6.96 (t, 2, J=5.6), 6.86 (br t, 2, J=5.1), 3.41 (q, 4, J=6.4), 3.35 (q, 4, J=6.2), 3.15-3.08 (quintet, 8), 1.38 (s, 18), 1.35 (s, 18); $^{13}$C NMR (DMSO-d$_6$) 165.43, 155.79, 155.50, 145.03, 125.70, 77.67, 77.52, 40.24 (overlaps with solvent), 39.05 (overlaps with solvent); RP-LC/MS (ESI) m/z 769.3 (M+H) % 791.3 (M+Na)$^+$ (t$_R$=5.10 min, 15-95% B). HRMS (ESI) m/z calcd for C$_{34}$H$_{61}$N$_{10}$O$_{10}$ (M+H)$^+$ 769.4567, found 769.4567.

I. 3,6-Bis[3-(benzyloxycarbonylamino)propylamino]-$N^2,N^5$-bis[2-(benzyloxycarbonyl)aminoethyl]pyrazine-2,5-dicarboxamide (16)

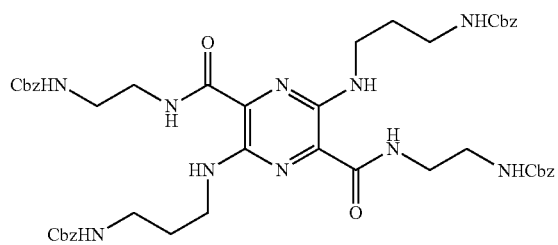

16

Step 1. Synthesis of 3,6-Diamino-$N^2,N^5$-bis[2-(benzyloxycarbonyl)aminoethyl]pyrazine-2,5-dicarboxamide (15)

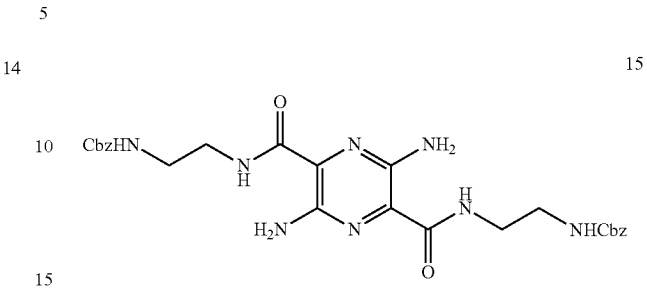

15

A suspension of N-carbobenzoxy-1,2-diaminoethane hydrochloride (4.61 g, 20.0 mmol) in anhyd DMF (100 mL) was stirred with DIPEA (3.50 mL, 20.1 mmol) for 30 min in an atmosphere of N$_2$. Then 3,6-diaminopyrazine-2,5-dicarboxylic acid (1.98 g, 10.0 mmol) was added, and after 15 min, HOBt.H$_2$O (3.37 g, 22.0 mmol) and EDC.HCl (4.22 g, 22.0 mmol) were added, and the resulting dark suspension was stirred at r.t. overnight (ca. 16 h). Most of the DMF was removed under high vacuum and the slurry was stirred with anhyd Et$_2$O-MeOH (1:3, v/v; 200 mL) for about 30 min. The precipitate was collected by filtration and thoroughly washed with MeOH and anhyd Et$_2$O and dried under high vacuum to give the bisamide 15 (4.37 g, 79%) as a yellow powder: $^1$H NMR (DMSO-d$_6$) 8.50 (t, 2, J=5.5), 7.39-7.31 (m, 10), 6.50 (br s, 4), 5.02 (s, 4), 3.37-3.34 (br q, 4), 3.20-3.17 (br q, 4); $^{13}$C NMR (DMSO-d$_6$) 165.80, 156.74, 146.65, 137.60, 128.78, 128.22, 128.20, 126.83, 65.74, 40.44 (overlaps with solvent), 39.22 (overlaps with solvent); RP-LC/MS (ESI) m/z 551.2 (M+H)$^+$, 573.2 (M+Na)$^+$ (t$_R$=3.86 min, 25-95% B). Anal. Calcd for C$_{26}$H$_{30}$N$_8$O$_6$: C, 56.72; H, 5.49, N, 20.35. Found: C, 56.79; H, 5.49; N, 20.30.

Step 2

To a yellow suspension of the above bisamide 15 (1.10 g, 2.00 mmol) in anhyd DCE (50 mL), 3-[(benzyloxycarbonyl)amino]propionaldehyde (1.24 g, 6.00 mmol) was added, and the reaction flask was immersed in an ice bath. Then HOAc (0.340 mL, 5.90 mmol) was added followed by the addition of sodium triacetoxyborohydride (1.27 g, 6.00 mmol) in small portions over a 30 min period. The resulting reddish suspension was slowly allowed to warm to r.t. and stirred overnight (ca. 40 h; RP-LC/MS analysis indicated some substrate) in an atmosphere of N$_2$. At this stage, the reaction mixture was diluted with anhyd DCE (30 mL) and treated with more 3-[(benzyloxycarbonyl)amino]propionaldehyde (0.414 g, 2.00 mmol), HOAc (0.12 mL, 2.08 mmol), and sodium triacetoxyborohydride (0.424 g, 2.00 mmol) as described above, and the reaction was continued over the weekend (RP-LC/MS analysis indicated only traces of substrate). After the usual work up described in Example 2, the crude product obtained was suspended in CH$_3$CN-anhyd Et$_2$O (1:1, v/v; 100 mL) and stirred at r.t. for 30 min. The precipitate was collected by filtration, washed with CH$_3$CN-anhyd Et$_2$O, and dried under high vacuum to give Example 9 (1.35 g) as an orange-red powder. The filtrate was concentrated and subjected to flash chromatography over silica gel [CHCl$_3$-MeOH (49:1, v/v)] to obtain additional 0.09 g of the product, bringing the overall yield to 1.44 g (77%): $R_f$ 0.42 [CHCl$_3$-MeOH (19:1, v/v)]; $^1$H NMR (DMSO-d$_6$) 8.53 (t, 2, J=5.5), 7.86 (br t, 2), 7.42 (t, 2, J=5.5), 7.36-7.21 (m, 20), 4.99 (s, 4), 4.98 (s, 4), 3.50-3.30

(m, 10), 3.18 (q, 4, J=6.1), 3.07 (q, 4, J=6.4), 1.66 (quintet, 4); RP-LC/MS (ESI) m/z 933.4 (M+H)⁺ (t$_R$=4.96 min, 15-95% B). Anal. Calcd for $C_{42}H_{68}N_8O_{12}$: C, 61.79; H, 6.05; N, 15.01. Found: C, 61.53; H, 5.92; N, 14.96.

J. Diethyl 3,6-bis(2-methoxyethylamino)pyrazine-2,5-dicarboxylate (17)

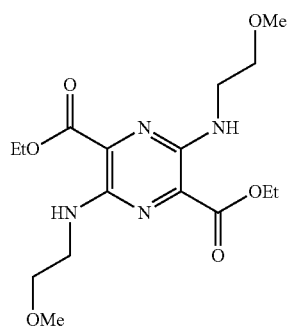

The reaction of diethyl 3,6-diaminopyrazine-2,5-dicarboxylate (0.127 g, 0.500 mmol)[2] with methoxyacetaldehyde (0.148 g, 2.00 mmol) in the presence of HOAc (0.115 mL, 2.00 mmol) and sodium triacetoxyborohydride (0.424 g, 2.00 mmol) in DCE (20 mL) was carried out as described in the preparation of Example 1. However, it should be mentioned here that the second batch of reagents were added after 21 h and the overall duration of the reaction was 68 h. After the usual work up, the red crude product (0.210 g) was subjected to flash chromatography over silica gel [$CH_2Cl_2$ to $CH_2Cl_2$-EtOAc (9:1, v/v)] to afford Example 10 (0.075 g, 41%) as a maroon solid: R$_f$ 0.29 [CHCl₃-EtOAc (19:1, v/v)]; ¹H NMR (CDCl₃) 7.31 (t, 2, J=5.3), 4.39 (q, 4, J=7.1), 3.69-3.60 (m, 8), 3.41 (s, 6), 1.41 (t, 6, J=7.1); ¹³C NMR (CDCl₃) 166.28, 147.48, 125.54, 71.41, 61.58, 58.76, 40.68, 14.14; RP-LC/MS (ESI) m/z 371.2 (M+H)⁺, 393.2 (M+Na)⁺ (t$_R$=4.59 min, 15-95% B).

K. 3,6-Bis(38-oxo-2,5,8,11,14,17,20,23,26,29,32,35-dodecaoxa-39-azahentetracontan-41-ylamino)-N², N⁵-bis(38-oxo-2,5,8,11,14,17,20,23,26,29,32,35-dodecaoxa-39-azahentetracontan-41-yl)pyrazine-2,5-dicarboxamide (18)

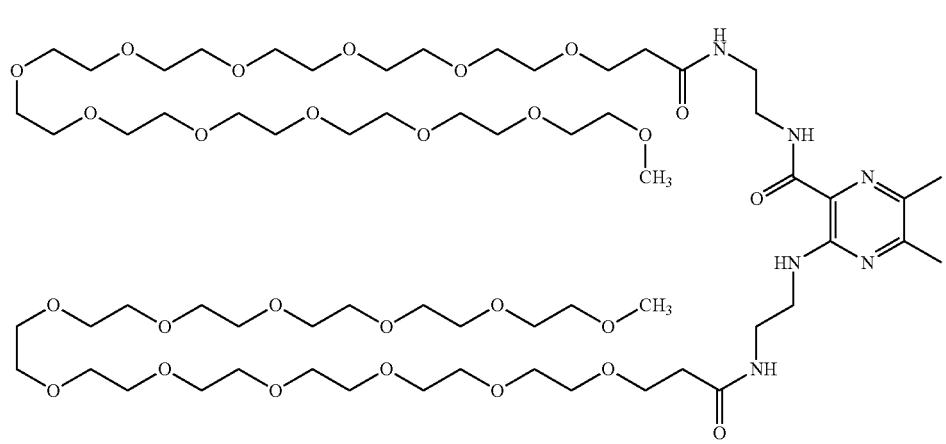

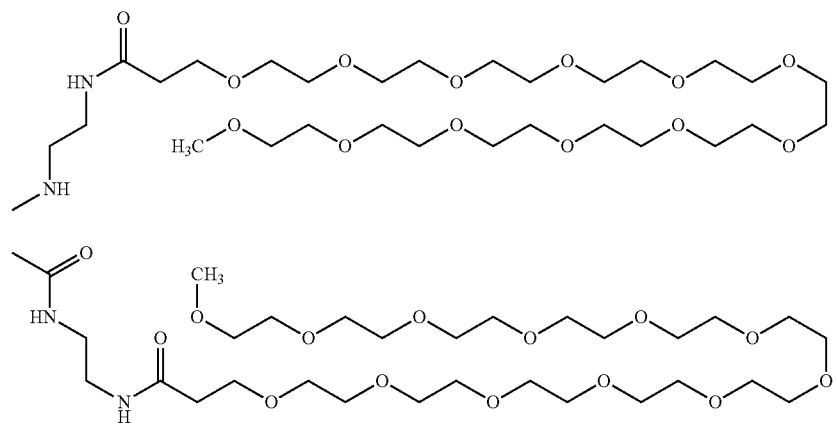

Compound 18, above, is a longer wavelength compound (excitation ~500 nm, emission 600 nm orange). To achieve the red shift in both excitation and emission wavelengths, electron donation into the ring was increased by alkyl substitution on the pyrazine ring nitrogens. The synthetic strategy for these longer wavelength analogues involves functionalizing the carboxyls first through amide chemistry described above followed by reductive amination of the pyrazine amino groups. Thus the synthesis of compound 18, above, is presented below. MP-3064 was coupled with Boc-ethylenediamine using the EDC method to afford MP-3183. This material was then converted to MP-3216 by reductive amination using Boc-2-aminoacetaldehyde and sodium triacetoxyborohydride. MP-3216 was purified by flash chromatography and deprotected with TFA to afford the corresponding tetramine salt. This material was then acylated with NHS-m-dPEG$_{12}$ and purified by HPLC to afford compound 18:

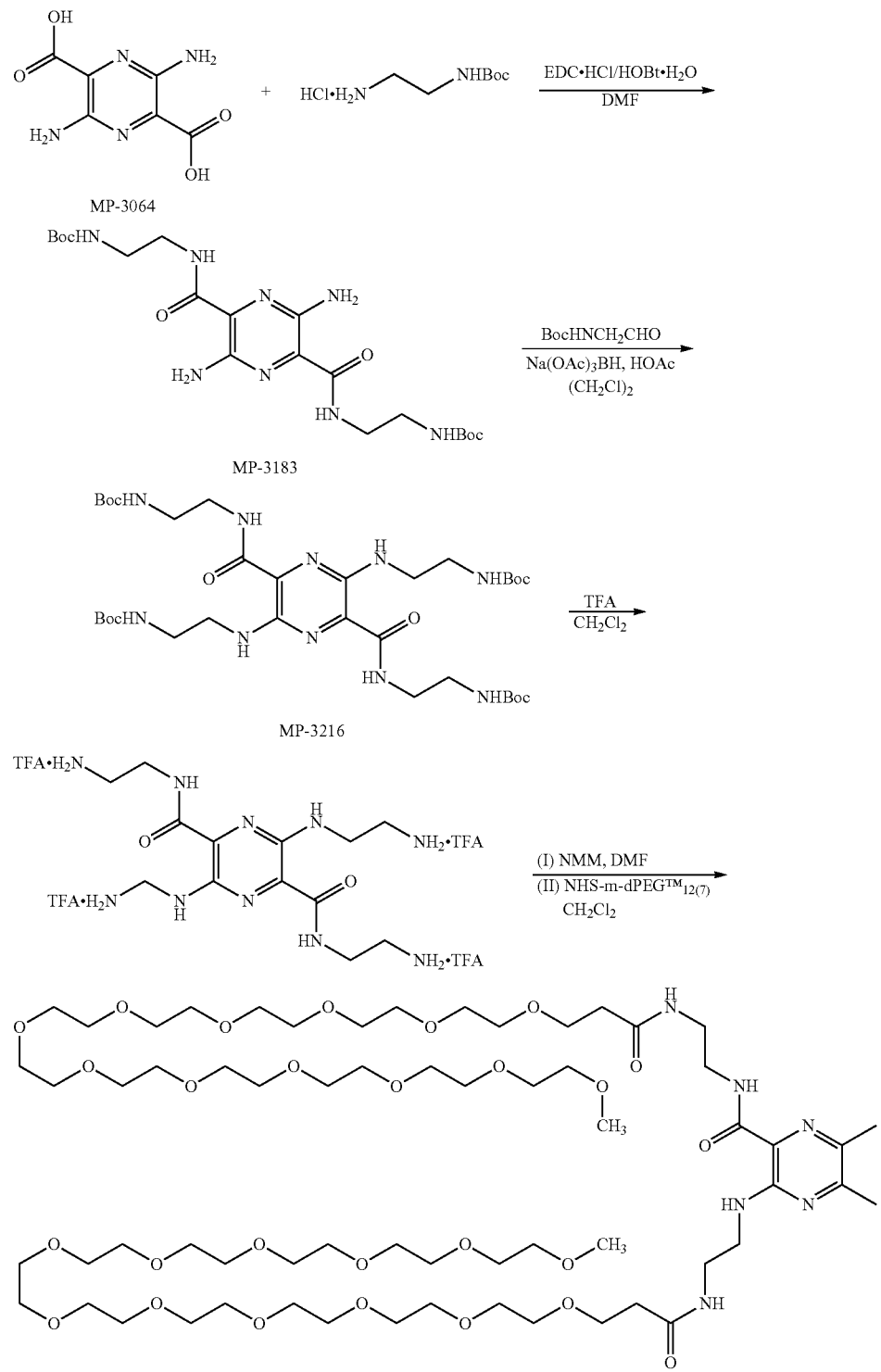

-continued

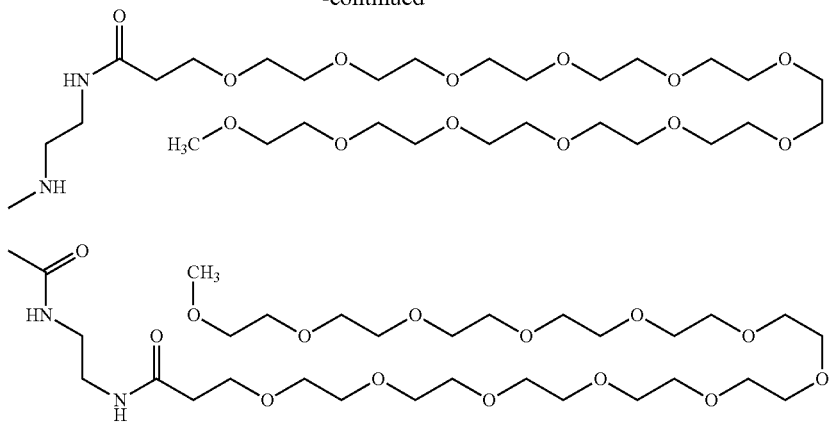

18

A mixture of sodium 3,6-diaminopyrazine-2,5-dicarboxylate (500 mg, 2.07 mmol), tert-butyl 2-aminoethylcarbamate (673 mg, 4.20 mmol), HOBt-H$_2$O (836 mg, 5.46 mmol) and EDC-HCl (1.05 g, 5.48 mmol) in DMF (25 mL) was stirred for 16 h and concentrated. The residue was partitioned with 1N NaHSO$_4$ (200 mL) and EtOAc (200 mL). The layers were separated and the organic was washed with water (200 mL), sat. NaHCO$_3$ (200 mL) and brine (200 mL). The EtOAc solution was dried (Mg$_2$SO$_4$), filtered and concentrated to afford 770 mg (76% yield) of 3,6-diamino-N$^2$,N$^5$-bis(2-(tert-butoxy carbonylaminoethyl))pyrazine-2,5-dicarboxamide (W-3183) as an orange foam: $^1$NMR (300 MHz, DMSO-d$_6$) major comformer, δ 8.44 (t, J=5.7 Hz, 2H), 6.90 (t, J=5.7 Hz, 2H), 6.48 (bs, 4H), 2.93-3.16 (complex m, 8H), 1.37 (s, 9H), 1.36 (s, 9H). $^{13}$C NMR (75 MHz, DMSO-d$_6$), conformational isomers δ 165.1 (s), 155.5 (bs), 155.4 (bs), 146.0 (s), 126.2 (s), 77.7 (bs), 77.5 (bs), 45.2 (bt), 44.5 (bt), 28.2 (q). LCMS (15-95% gradient ACN in 0.1% TFA over 10 min), single peak retention time=7.18 min on 30 mm column, (M+H)$^+$=483.

To a partially-dissolved yellow suspension of MP-3183 (0.483 g, 1.00 mmol) in anhydrous DCE (20 mL), N-Boc-2-aminoacetaldehyde (0.382 g, 2.40 mmol) was added, and the reaction flask was immersed in an ice bath. Then HOAc (0.120 mL, 2.08 mmol) was added followed by the addition of sodium triacetoxyborohydride (0.636 g, 3.00 mmol) in small portions over a 15 min period. The resulting reddish suspension was slowly allowed to warm to room temperature and stirred overnight (ca. 16 h; LC/MS analysis indicated some substrate). At this stage, the reaction mixture was treated with more N-Boc-2-aminoacetaldehyde (0.191 g, 1.20 mmol), HOAc (0.120 mL, 2.08 mmol), and sodium triacetoxyborohydride (0.212 g, 1.00 mmol) as described above, and the reaction was continued overnight (ca. 25 h; RP-LC/MS analysis indicated a complete reaction). The reaction was quenched by a slow addition of sat. NaHCO$_3$ (30 mL) at 0° C. The biphasic mixture was stirred for 30 min and extracted with CHCl$_3$ (3×40 mL). The combined organic extracts were washed with H$_2$O and brine (50 mL each). Removal of the solvent gave 1.04 g of a red solid, which upon flash chromatography over silica gel [CHCl$_3$-EtOAc (1:1, v/v)] afforded WP-3216 (0.813 g, quantitative) as brick-red solid: R$_f$ 0.27; $^1$H NMR (DMSO-d$_6$) δ 8.81 (t, 2, J=5.9), 7.95 (t, 2, J=5.9), 6.96 (t, 2, J=5.6), 6.86 (br t, 2, J=5.1), 3.41 (q, 4, J=6.4), 3.35 (q, 4, J=6.2), 3.15-3.08 (quintet, 8), 1.38 (s, 18), 1.35 (s, 18); $^{13}$C NMR (DMSO-d$_6$) δ 165.43, 155.79, 155.50, 145.03, 125.70, 77.67, 77.52, 40.24 (overlaps with solvent), 39.05 (overlaps with solvent); LC/MS (ESI) m/z 769.3 (M+H)$^+$, 791.3 (M+Na)$^+$ (t$_R$=5.10 min, 15-95% B). HRMS (ESI) m/z calcd for C$_{34}$H$_{61}$N$_{10}$O$_{10}$ (M+H)$^+$ 769.4567, found 769.4567.

To a red suspension of MP-3216 (0.769 g, 1.00 mmol) in anhyd CH$_2$Cl$_2$ (15 mL), was added TFA (15 mL) carefully while stirring at ice-bath temperature. The reaction became homogeneous instantaneously with a pale yellow coloration, and then turned red after a few minutes. After 30 min at 0° C., the cooling bath was removed, and the reaction continued for 1.5 h under N$_2$ atmosphere. The reaction mixture was concentrated in vacuo, the viscous residue was co-evaporated with CH$_2$Cl$_2$ (5×25 mL), and then dried overnight under high vacuum to give MP-3216-tfa salt (0.886 g, 107% for tetra-TFA salt) as a reddish brown solid: $^1$H NMR (DMSO-d$_6$) δ 8.75 (t, 2, J=6.1), 8.06 (br t, 2), 7.97 (br s, 4), 7.86 (br s, 4), 3.73 (br q, 4), 3.55 (q, 4, J=6.3), 3.04-2.95 (m, 8); RP-LC/MS (ESI) m/z 369.4 (M+H)$^+$, 737.4 (2M+H)$^+$ (t$_R$=1.09 min, 5-95% ACN in H$_2$O, 0.1% TFA).

To a red solution of the MP-3216-tfa salt (0.543 g crude, 0.50 mmol) in DMF (8 mL), NMM (1.10 mL, 10.0 mmol) was added at 0° C., and stirred for 30 min in an atmosphere of N$_2$. Then a solution of NHS-m-dPEG™$_{12}$ (7, 1.58 g, 2.30 mmol) in CH$_2$Cl$_2$ (2 mL) was added and the reaction mixture was stirred overnight (ca. 14 h) at ambient temperature. Most of the solvents were removed under high vacuum and the red syrup was subjected to preparative HPLC [column: Waters XBrdige™ Prep C18 OBD™ 5 μm 10×150 mm; λ$_{max}$: PDA (200-600 nm); flow: 50 mL/min; gradient: 5-50% B/10 min (mobile phase A: 0.1% TFA in H$_2$O; mobile phase B: 0.1% TFA in CH$_3$CN)] to give MP-3217 (0.443 g, 33%) as a brick-red slush: $^1$H NMR (DMSO-d$_6$) characteristic br s at δ 3.50 and s at δ 3.23 for poly(ethylene glycol) moiety; HPLC (254 nm) 89% [t$_R$=14.4 min, 20-80% ACN in H$_2$O, 0.1% TFA over 20 min (column: Phenomenex Luna 5 μm C18(2) 100 Å250× 4.6 mm; flow: 1 mL/min; mobile phase A: 0.1% TFA in H$_2$O; mobile phase B: 0.1% TFA in CH$_3$CN]; LC/MS (ESI) m/z 884.3 (M+3H)$^{3+}$, 1325.4 (M+21)$^{2+}$ (t$_R$=3.81 min, 5-95% B). HRMS (ESI) m/z calcd for C$_{118}$H$_{231}$N$_{10}$O$_{54}$ (M+3H)$^{3+}$ 884.1874, found 884.1872; calcd for C$_{118}$H$_{230}$N$_{10}$O$_{54}$ (M+2H)$^{2+}$ 1325.7774, found 1325.7769.

Other Aspects and Embodiments

The detailed description set forth above is provided to aid those skilled in the art in practicing the present invention.

However, the invention described and claimed herein is not to be limited in scope by the specific aspects and embodiments herein disclosed because these aspects and embodiments are intended as illustration of several aspects of the invention. Any equivalent aspects and embodiments are intended to be within the scope of this invention. Indeed, various modifications of the invention in addition to those shown and described herein will become apparent to those skilled in the art from the foregoing description that do not depart from the spirit or scope of the present inventive discovery. Such modifications are also intended to fall within the scope of the appended claims.

REFERENCES CITED

Citation of a reference herein shall not be construed as an admission that such is prior art to the present invention.

[1] C. A. Rabito, L. S. T. Fang, and A. C. Waltman, "Renal function in patients at risk with contrast material-induced acute renal failure: Noninvasive real-time monitoring," *Radiology* 1993, 186, 851-854.

[2] N. L. Tilney, and J. M. Lazarus, "Acute renal failure in surgical patients: Causes, clinical patterns, and care," *Surgical Clinics of North America* 1983, 63, 357-377.

[3] B. E. VanZee, W. E. Hoy, and J. R. Jaenike, "Renal injury associated with intravenous pyelography in non-diabetic and diabetic patients," *Annals of Internal Medicine* 1978, 89, 51-54.

[4] S. Lundqvist, G. Edbom, S. Groth, U. Stendahl and S.-O. Hietala, "Iohexyl clearance for renal function measurement in gynecologic cancer patients," *Acta Radiologica* 1996, 37, 582-586.

[5] P. Guesry, L. Kaufman, S. Orloff, J. A. Nelson, S. Swann, and M. Holliday, "Measurement of glomerular filtration rate by fluorescent excitation of non-radioactive meglumine iothalamate," *Clinical Nephrology* 1975, 3, 134-138.

[6] C. C. Baker, L. Oppenheimer, and B. Stephens, "Epidemiology of trauma deaths," *American Journal of Surgery* 1980, 140, 144-150.

[7] R. G. Lobenhoffer, and M. Grotz, "Treatment results of patients with multiple trauma: An analysis of 3406 cases treated between 1972 and 1991 at a German level I trauma center," *Journal of Trauma* 1995, 38, 70-77.

[8] F. W. Dodge, B. L Travis, and C. N. Daeschner, "Comparison of endogenous creatinine clearance with inulin clearance," *Am. J. Dis. Child.* 1967, 113, 683-692.

[9] J. Brochner-Mortensen, J. Giese, N. Rossing, "Renal inulin clearance versus total plasma clearance of $^{51}$Cr-EDTA," *Scand J. Clin. Lab. Invest.* 1969, 23, 301-303.

[10] C. White, C. Akbari, N. Hussain, L. Dinh, G. Filler, N. Lepage, and G. Knoll, "Estimating glomerular filtration rate in kidney transplantation: A comparison between serum creatinine and cystatin C-based methods," *J. Am. Soc. Nephrol,* 2005, 16, 3763-3770 and references cited therein.

[11] P. L. Choyke, H. A. Austin, J. A. Frank, "Hydrated clearance of gadolinium-DTPA as a measurement of glomerular filtration rate," *Kidney International* 1992, 41, 1595-1598.

[12] M. F. Tweedle, X. Zbang, M. Fernandez, P. Wedeking, A. D. Nunn, and H. W. Strauss, "A noninvasive method for monitoring renal status at the bedside," *Invest. Radiol.* 1997, 32, 802-805.

[13] N. Lewis, R. Kerr, C. Van Buren, "Comparative evaluation of urographic contrast media, inulin, and $^{99m}$Tc-DTPA clearance methods for determination of glomerular filtration rate in clinical transplantation," *Transplantation* 1989, 48, 790-796.

[14] R. Muller-Suur, C. Muller-Suur, "Glomerular filtration and tubular secretion of $MAG_3$ in rat kidney," *Journal of Nuclear Medicine* 1989, 30, 1986-1991.

[15] Sekar, N. Pyrazine dyes: An update. *Colourage* 1999, 41-44.

[16] Shirai, K.; Yanagisawa, A.; Takahashi, H.; Fukunishi, K.; Matsuoka, M. "Syntheses and fluorescent properties of 2,5-diamino-3,6-dicyanopyrazine dyes," *Dyes and Pigments* 1998, 39, 49-68.

[17] Kim, J. H.; Shin, S. R.; Matsuoaka, M.; Fukunishi, K. "Self-assembling of aminopyrazine fluorescent dyes and their solid state spectra," *Dyes and Pigments* 1998, 39, 341-357.

[18] Kim, J. H.; Shin, S. R.; Matsuoaka, M.; Fukunishi, K. Self-assembling of aminopyrazine fluorescent dyes and their solid state spectra, Part 2. *Dyes and Pigments* 1999, 41, 183-191.

[19] F. Roch-Ramel, K. Besseghir, and H. Murer. Renal excretion and tubular transport of organic anions and cations. In *Handbook of Physiology, Section 8, Neurological Physiology*, Vol. II, E. E. Windhager, Editor, pp. 2189-2262. Oxford University Press: New York, 1992

[20] F. Roch-Ramel and M. E. De Broe, Chapter 2, "Renal handling of drugs and xenobiotics," in *Clinical Nephrotoxins: Renal Injury from Drugs and Chemicals*, M. E. De Broe, G. Porter, W. Bennett, G. Verpooten Eds., pp 21-46, Kluwer Academic Publishers, Dordrecht, The Netherlands, 2003.

[21] Yamaoka, T., Tabata, Y., Ikada, Y. J. Pharm. Sci. 1994, 83, 601.

[22] Muller et al. Eds, Medical Optical Tomography, SPE Volume IS11, 1993.

[23] R. B. Dorshow et al. Non-Invasive Fluorescence Detection of Hepatic and Renal Function, Bull. Am. Phys. Soc. 1997, 42, 681.

What is claimed is:
1. A compound of the Formula I:

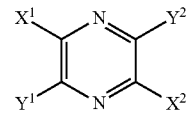

Formula I; wherein
each of $X^1$ and $X^2$ is independently $-CONR^7R^9$;
each of $Y^1$ and $Y^2$ is independently $-NR^{48}R^{49}$;
each $R^7$ is independently $-(CH_2)_a(CH_2CH_2O)_b(CH_2)_cNR^{10}CONR^{11}(CH_2)_d(CH_2CH_2O)_eR^{20}$,
$-(CH_2)_a(CH_2CH_2O)_b(CH_2)_cNR^{12}CSNR^{13}(CH_2)_d(CH_2CH_2O)_eR^{21}$, $-(CH_2)_a(CH_2CH_2O)_b(CH_2)_cCONR^{14}(CH_2)_d(CH_2CH_2O)_eR^{22}$, $-(CH_2)_a(CH_2CH_2O)_b(CH_2)_cNR^{15}SO_2(CH_2)_d(CH_2CH_2O)_eR^{23}$,
$-(CH_2)_a(CH_2CH_2O)_b(CH_2)_cSO_2NR^{16}(CH_2)_d(CH_2CH_2O)_eR^{24}$, $-(CH_2)_a(CH_2CH_2O)_b(CH_2)_cNR^{17}CO(CH_2)_d(CH_2CH_2O)_eR^{25}$, $-(CH_2)_a(CH_2CH_2O)_b(CH_2)_cNR^{18}CO_2(CH_2)_d(CH_2CH_2O)_eR^{26}$,
or $-(CH_2)_a(CH_2CH_2O)_b(CH_2)_cOC(O)NR^{19}CO_2(CH_2)_d(CH_2CH_2O)_eR^{27}$;
each $R^{48}$ is independently $-(CH_2)_cOR^{68}$, $-CH_2(CHOH)_cR^{69}$, $-CH_2(CHOH)_cCO_2H$, $-(CHCO_2H)_cCO_2H$, $-(CH_2)_cNR^{70}R^{71}$, $-CH[(CH_2)_cNH_2]_cCO_2H$, $-CH[(CH_2)_cNH_2]_cCH_2OH$, $-CH_2(CHNH_2)_cCH_2NR^{72}R^{73}$, —(CH$_2$CH$_2$O)$_e$R$^{74}$, —(CH$_2$)$_t$CO(CH$_2$CH$_2$O)$_e$R$^{75}$, —(CH$_2$)$_u$(CH$_2$CH$_2$O)$_j$(CH$_2$)$_k$NR$^{58}$C(O)NR$^{59}$(CH$_2$)$_l$(CH$_2$CH$_2$O)$_o$R$^{76}$, —(CH$_2$)$_u$(CH$_2$CH$_2$O)$_j$(CH$_2$)$_k$NR$^{60}$C(S)NR$^{61}$(CH$_2$)$_l$(CH$_2$CH$_2$O)$_o$R$^{77}$, —(CH$_2$)$_u$(CH$_2$CH$_2$O)$_j$(CH$_2$)$_k$C(O)NR$^{62}$(CH$_2$)$_l$(CH$_2$CH$_2$O)$_o$R$^{78}$, —(CH$_2$)$_u$(CH$_2$CH$_2$O)$_j$(CH$_2$)$_k$S(O)$_2$NR$^{63}$(CH$_2$)$_l$(CH$_2$CH$_2$O)$_o$R$^{79}$, —(CH$_2$)$_u$(CH$_2$CH$_2$O)$_j$(CH$_2$)$_k$NR$^{64}$S(O)$_2$(CH$_2$)$_l$(CH$_2$CH$_2$O)$_o$R$^{80}$, —(CH$_2$)$_u$(CH$_2$CH$_2$O)$_j$(CH$_2$)$_k$NR$^{65}$C(O)(CH$_2$)$_l$(CH$_2$CH$_2$O)$_o$R$^{81}$, —(CH$_2$)$_u$(CH$_2$CH$_2$O)$_j$(CH$_2$)$_k$NR$^{66}$C(O)O(CH$_2$)$_l$(CH$_2$CH$_2$O)$_o$R$^{82}$, or —(CH$_2$)$_u$(CH$_2$CH$_2$O)$_j$(CH$_2$)$_k$OC(O)NR$^{67}$(CH$_2$)$_l$(CH$_2$CH$_2$O)$_o$R$^{83}$, —(CH$_2$)$_a$SO$_3$H, —(CH$_2$)$_a$SO$_3^-$, —(CH$_2$)$_a$OSO$_3$H, —(CH$_2$)$_a$OSO$_3^-$, —(CH$_2$)$_a$NHSO$_3$H, —(CH$_2$)$_a$NHSO$_3^-$, —(CH$_2$)$_a$PO$_3$H$_2$, —(CH$_2$)$_a$PO$_3$H$^-$, —(CH$_2$)$_a$PO$_3^=$, —(CH$_2$)$_a$OPO$_3$H$_2$, —(CH$_2$)$_a$OPO$_3$H$^-$, or —(CH$_2$)$_a$OPO$_3$;

each R$^{49}$ is independently —H, —(CH$_2$)$_c$OR$^{68}$, —CH$_2$(CHOH)$_c$R$^{69}$, —CH$_2$(CHOH)$_c$CO$_2$H, —(CHCO$_2$H)$_c$CO$_2$H, —(CH$_2$)$_c$NR$^{70}$R$^{71}$, —CH[(CH$_2$)$_c$NH$_2$]$_c$CO$_2$H, —CH[(CH$_2$)$_c$NH$_2$]$_c$CH$_2$OH, —CH$_2$(CHNH$_2$)$_c$CH$_2$NR$^{72}$R$^{73}$, —(CH$_2$CH$_2$O)$_e$R$^{74}$, —(CH$_2$)$_c$CO(CH$_2$CH$_2$O)$_e$R$^{75}$, —(CH$_2$)$_i$(CH$_2$CH$_2$O)$_j$(CH$_2$)$_k$NR$^{58}$C(O)NR$^{59}$(CH$_2$)$_l$(CH$_2$CH$_2$O)$_o$R$^{76}$, —(CH$_2$)$_i$(CH$_2$CH$_2$O)$_j$(CH$_2$)$_k$NR$^{60}$C(S)NR$^{61}$(CH$_2$)$_l$(CH$_2$CH$_2$O)$_o$R$^{77}$, —(CH$_2$)$_i$(CH$_2$CH$_2$O)$_j$(CH$_2$)$_k$C(O)NR$^{62}$(CH$_2$)$_l$(CH$_2$CH$_2$O)$_o$R$^{78}$, —(CH$_2$)$_i$(CH$_2$CH$_2$O)$_j$(CH$_2$)$_k$S(O)$_2$NR$^{63}$(CH$_2$)$_l$(CH$_2$CH$_2$O)$_o$R$^{79}$, —(CH$_2$)$_i$(CH$_2$CH$_2$O)$_j$(CH$_2$)$_k$NR$^{64}$S(O)$_2$(CH$_2$)$_l$(CH$_2$CH$_2$O)$_o$R$^{80}$, —(CH$_2$)$_i$(CH$_2$CH$_2$O)$_j$(CH$_2$)$_k$NR$^{65}$C(O)(CH$_2$)$_l$(CH$_2$CH$_2$O)$_o$R$^{81}$, —(CH$_2$)$_i$(CH$_2$CH$_2$O)$_j$(CH$_2$)$_k$NR$^{66}$C(O)O(CH$_2$)$_l$(CH$_2$CH$_2$O)$_o$R$^{82}$, —(CH$_2$)$_i$(CH$_2$CH$_2$O)$_j$(CH$_2$)$_k$OC(O)NR$^{67}$(CH$_2$)$_l$(CH$_2$CH$_2$O)$_o$R$^{83}$, —(CH$_2$)$_a$SO$_3$H, —(CH$_2$)$_a$SO$_3^-$, —(CH$_2$)$_a$OSO$_3$H, —(CH$_2$)$_a$OSO$_3^-$, —(CH$_2$)$_a$NHSO$_3$H, —(CH$_2$)$_a$NHSO$_3^-$, —(CH$_2$)$_a$PO$_3$H$_2$, —(CH$_2$)$_a$PO$_3$H$^-$, —(CH$_2$)$_a$PO$_3^=$, —(CH$_2$)$_a$OPO$_3$H$_2$, —(CH$_2$)$_a$OPO$_3$H$^-$, or —(CH$_2$)$_a$OPO$_3$;

each of R$^9$, R$^{10}$, R$^{11}$, R$^{12}$, R$^{13}$, R$^{14}$, R$^{15}$, R$^{16}$, R$^{17}$, R$^{18}$, and R$^{19}$ is independently —H or —CH$_3$;

each of R$^{20}$, R$^{21}$, R$^{22}$, R$^{23}$, R$^{24}$, R$^{25}$, R$^{26}$, and R$^{27}$ is independently —H, —CH$_3$, —(CH$_2$)$_g$NR$^{28}$C(O)NR$^{29}$(CH$_2$)$_g$(CH$_2$CH$_2$O)$_h$R$^{38}$, —(CH$_2$)$_g$NR$^{30}$CSNR$^{31}$(CH$_2$)$_g$(CH$_2$CH$_2$O)$_h$R$^{39}$, —(CH$_2$)$_g$C(O)NR$^{32}$(CH$_2$)$_g$(CH$_2$CH$_2$O)$_h$R$^{40}$, —(CH$_2$)$_g$S(O)$_2$NR$^{33}$(CH$_2$)$_g$(CH$_2$CH$_2$O)$_h$R$^{41}$, —(CH$_2$)$_g$NR$^{34}$S(O)$_2$(CH$_2$)$_g$(CH$_2$CH$_2$O)$_h$R$^{42}$, —(CH$_2$)$_g$NR$^{35}$C(O)(CH$_2$)$_g$(CH$_2$CH$_2$O)$_h$R$^{43}$, —(CH$_2$)$_g$NR$^{36}$C(O)O(CH$_2$)$_g$(CH$_2$CH$_2$O)$_h$R$^{44}$, —(CH$_2$)$_g$OC(O)NR$^{37}$(CH$_2$)$_g$(CH$_2$CH$_2$O)$_h$R$^{45}$, —CO(AA), or —CONH(PS);

each of R$^{28}$, R$^{29}$, R$^{30}$, R$^{31}$, R$^{32}$, R$^{33}$, R$^{34}$, R$^{35}$, R$^{36}$, and R$^{37}$ is independently —H or —CH$_3$;

each of R$^{38}$, R$^{39}$, R$^{40}$, R$^{41}$, R$^{42}$, R$^{43}$, R$^{44}$, to and R$^{45}$ is independently —H, —CH$_3$, —CO(AA) or —CONH(PS);

each of R$^{58}$, R$^{59}$, R$^{60}$, R$^{61}$, R$^{62}$, R$^{63}$, R$^{64}$, R$^{65}$, R$^{66}$, and R$^{67}$ is independently, —H or —CH$_3$;

each of R$^{68}$, R$^{69}$, R$^{70}$, R$^{71}$, R$^{72}$, R$^{73}$, R$^{74}$, R$^{75}$, R$^{76}$, R$^{77}$, R$^{78}$, R$^{79}$, and R$^{80}$ is independently —H, —CH$_3$, —(CH$_2$)$_p$S(O)$_2$NR$^{84}$(CH$_2$)$_q$(CH$_2$CH$_2$O)$_s$R$^{81}$, —(CH$_2$)$_p$NR$^{85}$S(O)$_2$(CH$_2$)$_q$(CH$_2$CH$_2$O)$_s$R$^{83}$, —(CH$_2$)$_p$NR$^{86}$C(O)(CH$_2$)$_q$(CH$_2$CH$_2$O)$_s$R$^{85}$, —(CH$_2$)$_p$NR$^{86}$C(O)O(CH$_2$)$_q$(CH$_2$CH$_2$O)$_s$R$^{87}$, or —(CH$_2$)$_p$OC(O)NR$^{88}$(CH$_2$)$_q$(CH$_2$CH$_2$O)$_s$R$^{89}$;

each of R$^{81}$, R$^{82}$, R$^{83}$, R$^{84}$, R$^{85}$, R$^{86}$, R$^{87}$, R$^{88}$, and R$^{89}$ is independently —H or —CH$_3$;

each (AA) is independently a polypeptide chain that includes one or more natural or unnatural α-amino acids linked together by peptide bonds;

each (PS) is independently a sulfated or non-sulfated polysaccharide chain comprising one or more monosaccharide units connected by glycosidic linkages;

each of 't' and 'u' is independently 1, 2, 3, 4, or 5;

each of 'a', 'd', 'g', 'i', 'l', and 'q' is independently 0, 1, 2, 3, 4, 5, 6, 7, 8, 9 or 10;

each of 'c', 'f', 'k', and 'p' is independently 0, 1, 2, 3, 4, 5, 6, 7, 8, 9 or 10; and each of 'b', 'j', 'e', 'h', 'o', and 's' is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100.

2. The compound of claim 1, wherein R$^7$ is independently —(CH$_2$)$_a$(CH$_2$CH$_2$O)$_b$(CH$_2$)$_c$NR$^{10}$CONR$^{11}$(CH$_2$)$_d$(CH$_2$CH$_2$O)$_e$R$^{20}$, —(CH$_2$)$_a$(CH$_2$CH$_2$O)$_b$(CH$_2$)$_c$CONR$^{14}$(CH$_2$)$_d$(CH$_2$CH$_2$O)$_e$R$^{22}$, —(CH$_2$)$_a$(CH$_2$CH$_2$O)$_b$(CH$_2$)$_c$NR$^{15}$SO$_2$(CH$_2$)$_d$(CH$_2$CH$_2$O)$_e$R$^{23}$, —(CH$_2$)$_a$(CH$_2$CH$_2$O)$_b$(CH$_2$)$_c$SO$_2$NR$^{16}$(CH$_2$)$_d$(CH$_2$CH$_2$O)$_e$R$^{24}$, —(CH$_2$)$_a$(CH$_2$CH$_2$O)$_b$(CH$_2$)$_c$NR$^{17}$CO(CH$_2$)$_d$(CH$_2$CH$_2$O)$_e$R$^{25}$, —(CH$_2$)$_a$(CH$_2$CH$_2$O)$_b$(CH$_2$)$_c$NR$^{18}$CO$_2$(CH$_2$)$_d$(CH$_2$CH$_2$O)$_e$R$^{26}$, or —(CH$_2$)$_a$(CH$_2$CH$_2$O)$_b$(CH$_2$)$_c$OC(O)NR$^{19}$CO$_2$(CH$_2$)$_d$(CH$_2$CH$_2$O)$_e$R$^{27}$.

3. The compound of claim 1, wherein R$^7$ is independently —(CH$_2$)$_a$(CH$_2$CH$_2$O)$_b$(CH$_2$)$_c$NR$^{10}$CONR$^{11}$(CH$_2$)$_d$(CH$_2$CH$_2$O)$_e$R$^{20}$, —(CH$_2$)$_a$(CH$_2$CH$_2$O)$_b$(CH$_2$)$_c$NR$^{12}$CSNR$^{13}$(CH$_2$)$_d$(CH$_2$CH$_2$O)$_e$R$^{21}$, —(CH$_2$)$_a$(CH$_2$CH$_2$O)$_b$(CH$_2$)$_c$CONR$^{14}$(CH$_2$)$_d$(CH$_2$CH$_2$O)$_e$R$^{22}$, —(CH$_2$)$_a$(CH$_2$CH$_2$O)$_b$(CH$_2$)$_c$NR$^{15}$SO$_2$(CH$_2$)$_d$(CH$_2$CH$_2$O)$_e$R$^{23}$, —(CH$_2$)$_a$(CH$_2$CH$_2$O)$_b$(CH$_2$)$_c$SO$_2$NR$^{16}$(CH$_2$)$_d$(CH$_2$CH$_2$O)$_e$R$^{24}$, —(CH$_2$)$_a$(CH$_2$CH$_2$O)$_b$(CH$_2$)$_c$NR$^{18}$CO$_2$(CH$_2$)$_d$(CH$_2$CH$_2$O)$_e$R$^{26}$, or —(CH$_2$)$_a$(CH$_2$CH$_2$O)$_b$(CH$_2$)$_c$OC(O)NR$^{19}$CO$_2$(CH$_2$)$_d$(CH$_2$CH$_2$O)$_e$R$^{27}$.

4. The compound of claim 1, wherein:
each of R$^{20}$, R$^{21}$, R$^{22}$, R$^{23}$, R$^{24}$, R$^{25}$, R$^{26}$, and R$^{27}$ is independently —H, —CH$_3$, —(CH$_2$)$_g$NR$^{28}$C(O)NR$^{29}$(CH$_2$)$_g$(CH$_2$CH$_2$O)$_h$R$^{38}$, —(CH$_2$)$_g$NR$^{30}$CSNR$^{31}$(CH$_2$)$_g$(CH$_2$CH$_2$O)$_h$R$^{39}$, —(CH$_2$)$_g$C(O)NR$^{32}$(CH$_2$)$_g$(CH$_2$CH$_2$O)$_h$R$^{40}$, —(CH$_2$)$_g$S(O)$_2$NR$^{33}$(CH$_2$)$_g$(CH$_2$CH$_2$O)$_h$R$^{41}$, —(CH$_2$)$_g$NR$^{34}$S(O)$_2$(CH$_2$)$_g$(CH$_2$CH$_2$O)$_h$R$^{42}$, —(CH$_2$)$_g$NR$^{36}$C(O)O(CH$_2$)$_g$(CH$_2$CH$_2$O)$_h$R$^{44}$, —(CH$_2$)$_g$OC(O)NR$^{37}$(CH$_2$)$_g$(CH$_2$CH$_2$O)$_h$R$^{45}$, —CO(AA), or —CONH(PS).

5. The compound of claim 1, wherein each of R$^{31}$, R$^{32}$, R$^{33}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, and R$^{45}$ is independently —H or —CH$_3$.

6. The compound of claim 1, wherein:
each R$^{48}$ is independently —(CH$_2$)$_c$OR$^{68}$, —CH$_2$(CHOH)$_c$R$^{69}$, —CH$_2$(CHOH)$_c$CO$_2$H, —(CHCO$_2$H)$_c$CO$_2$H, —(CH$_2$)$_c$NR$^{70}$R$^{71}$, —CH[(CH$_2$)$_c$NH$_2$]$_c$CO$_2$H, —CH[(CH$_2$)$_c$NH$_2$]$_c$CH$_2$OH, —CH$_2$(CHNH$_2$)$_c$CH$_2$NR$^{72}$R$^{73}$, —(CH$_2$CH$_2$O)$_e$R$^{74}$, —(CH$_2$)$_c$CO(CH$_2$CH$_2$O)$_e$R$^{75}$, —(CH$_2$)$_u$(CH$_2$CH$_2$O)$_j$(CH$_2$)$_k$NR$^{58}$C(O)NR$^{59}$(CH$_2$)$_l$(CH$_2$CH$_2$O)$_o$R$^{76}$, —(CH$_2$)$_u$(CH$_2$CH$_2$O)$_j$(CH$_2$)$_k$NR$^{60}$C(S)NR$^{61}$(CH$_2$)$_l$(CH$_2$CH$_2$O)$_o$R$^{77}$, —(CH$_2$)$_u$(CH$_2$CH$_2$O)$_j$(CH$_2$)$_k$C(O)NR$^{62}$(CH$_2$)$_l$(CH$_2$CH$_2$O)$_o$R$^{78}$, —(CH$_2$)$_u$(CH$_2$CH$_2$O)$_j$(CH$_2$)$_k$S(O)$_2$NR$^{63}$(CH$_2$)$_l$(CH$_2$CH$_2$O)$_o$R$^{79}$, —(CH$_2$)$_u$(CH$_2$CH$_2$O)$_j$(CH$_2$)$_k$NR$^{64}$S(O)$_2$(CH$_2$)$_l$(CH$_2$CH$_2$O)$_o$R$^{80}$, —(CH$_2$)$_u$(CH$_2$CH$_2$O)$_j$(CH$_2$)$_k$NR$^{65}$C(O)(CH$_2$)$_l$(CH$_2$CH$_2$O)$_o$R$^{81}$, —(CH$_2$)$_u$(CH$_2$CH$_2$O)$_j$(CH$_2$)$_k$NR$^{66}$C(O)O(CH$_2$)$_l$(CH$_2$CH$_2$O)$_o$R$^{82}$, or —(CH$_2$)$_u$(CH$_2$CH$_2$O)$_j$(CH$_2$)$_k$OC(O)NR$^{67}$(CH$_2$)$_l$(CH$_2$CH$_2$O)$_o$R$^{83}$, —(CH$_2$)$_a$SO$_3$H, —(CH$_2$)$_a$SO$_3^-$, —(CH$_2$)$_a$OSO$_3$H, —(CH$_2$)$_a$OSO$_3^-$, —(CH$_2$)$_a$NHSO$_3$H, or —(CH$_2$)$_a$NHSO$_3^-$; and each R$^{49}$ is independently —H, —(CH$_2$)$_c$OR$^{68}$, —CH$_2$(CHOH)$_c$R$^{69}$, —CH$_2$(CHOH)$_c$CO$_2$H, —(CHCO$_2$H)$_c$CO$_2$H, —(CH$_2$)$_c$NR$^{70}$R$^{71}$, —CH[(CH$_2$)$_f$NH$_2$]$_c$CO$_2$H, —CH[(CH$_2$)$_f$NH$_2$]$_c$CH$_2$OH, —CH$_2$(CHNH$_2$)$_c$CH$_2$NR$^{72}$R$^{73}$, —(CH$_2$CH$_2$O)$_e$R$^{74}$, —(CH$_2$)$_c$CO(CH$_2$CH$_2$O)$_e$R$^{75}$, —(CH$_2$)$_i$(CH$_2$CH$_2$O)$_j$(CH$_2$)$_k$NR$^{58}$C(O)NR$^{59}$(CH$_2$)$_l$(CH$_2$CH$_2$O)$_o$R$^{76}$, —(CH$_2$)$_i$(CH$_2$CH$_2$O)$_j$(CH$_2$)$_k$NR$^{60}$C(S)NR$^{61}$(CH$_2$)$_l$(CH$_2$CH$_2$O)$_o$R$^{77}$, —(CH$_2$)$_i$(CH$_2$CH$_2$O)$_j$(CH$_2$)$_k$C(O)NR$^{62}$(CH$_2$)$_l$(CH$_2$CH$_2$O)$_o$R$^{78}$, —(CH$_2$)$_i$(CH$_2$CH$_2$O)$_j$(CH$_2$)$_k$S(O)$_2$NR$^{63}$(CH$_2$)$_l$(CH$_2$CH$_2$O)$_o$R$^{79}$, —(CH$_2$)$_i$(CH$_2$CH$_2$O)$_j$(CH$_2$)$_k$NR$^{64}$S(O)$_2$(CH$_2$)$_l$(CH$_2$CH$_2$O)$_o$R$^{80}$, —(CH$_2$)$_i$(CH$_2$CH$_2$O)$_j$(CH$_2$)$_k$NR$^{65}$C(O)(CH$_2$)$_l$(CH$_2$CH$_2$O)$_o$R$^{81}$, —(CH$_2$)$_i$(CH$_2$CH$_2$O)$_j$(CH$_2$)$_k$NR$^{66}$C(O)O(CH$_2$)$_l$(CH$_2$CH$_2$O)$_o$R$^{82}$, —(CH$_2$)$_i$(CH$_2$CH$_2$O)$_j$(CH$_2$)$_k$OC(O)NR$^{67}$(CH$_2$)$_l$(CH$_2$CH$_2$O)$_o$R$^{83}$, —(CH$_2$)$_a$SO$_3$H, —(CH$_2$)$_a$SO$_3^-$, —(CH$_2$)$_a$OSO$_3$H, —(CH$_2$)$_a$OSO$_3^-$, —(CH$_2$)$_a$NHSO$_3$H, or —(CH$_2$)$_a$NHSO$_3^-$.

7. The compound of claim 1, wherein:
each of 'a', 'd', 'g', 'i' and 'q' is independently 0, 1, 2, 3, 4, 5, or 6.

8. The compound of claim 1, wherein:
each of 'e', 'h', 'o', and 's' is independently 0, 1, 2, 3, 4, 5, 6, 7, 8, 9, 10, 11, 12, 13, 14, 15, 16, 17, 18, 19, or 20.

9. The compound of claim 1, wherein:
each of 'b' and 'j' is independently 0, 1, 2, 3, 4, 5, 6, 7, 8, 9, 10, 11, 12, 13, 14, 15, 16, 17, 18, 19, or 20.

10. The compound of claim 1 having a molecular weight of no more than 20000.

11. The compound of claim 1 having a molecular weight of no more than 15000, 14000, 13000, 12000, 11000, 10000, 9000, 8000, 7000, 6000, 5000, 4500, 4000, 3500, 3000, 2500, 2000, 1500, 1000, 900, 800, 700, 600, 500, 400, 300, 200, or 100.

12. The compound of claim 1 having a molecular weight that is greater than 20000.

13. The compound of claim 1 wherein each of 't' and 'u' is independently 2, 3, 4, or 5.

14. The compound of claim 1 wherein each of 't' and 'u' is independently 2.

15. The compound of claim 1 wherein each of 'a' is independently 2, 3, 4, or 5.

16. The compound of claim 1 wherein each of 'a' is independently 2.

17. A method of using the compound of claim 1, the method comprising:
administering a compound of claim 1 into a body of a patient;
exposing the compound to visible and/or near infrared light while the compound is in the body of the patient; and
detecting spectral energy emanating from the compound while the compound is in the body of the patient, wherein the compound emanates spectral energy due to the exposing.

18. The method of claim 17, further comprising determining renal function of the patient based on the detecting.

19. A compound of the following structure:

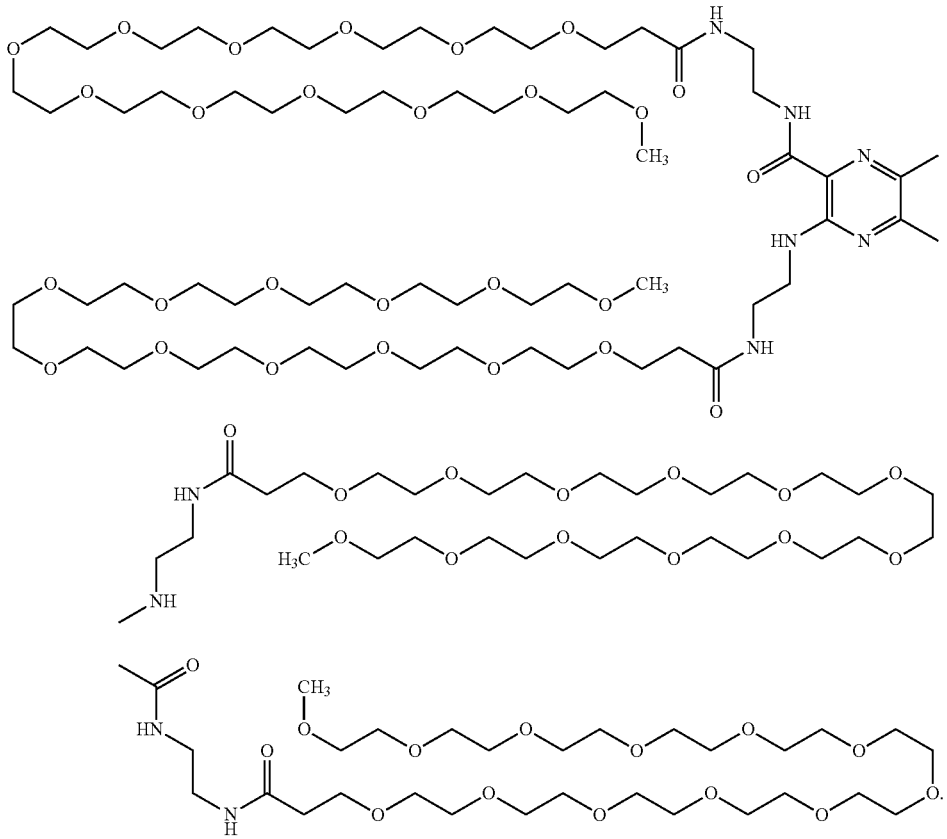

* * * * *